US011864605B2

(12) United States Patent
Bentley

(10) Patent No.: US 11,864,605 B2
(45) Date of Patent: *Jan. 9, 2024

(54) MEDICAL APPARATUS

(71) Applicant: Ben Guard Healthcare Solutions LLC, Cincinnati, OH (US)

(72) Inventor: Rhonda McPartland Bentley, Cincinnati, OH (US)

(73) Assignee: Concinnity Medical Devices, Inc., Wilmington, DE (US)

( * ) Notice: Subject to any disclaimer, the term of this patent is extended or adjusted under 35 U.S.C. 154(b) by 44 days.

This patent is subject to a terminal disclaimer.

(21) Appl. No.: 17/986,266

(22) Filed: Nov. 14, 2022

(65) Prior Publication Data

US 2023/0070019 A1 Mar. 9, 2023

Related U.S. Application Data

(63) Continuation of application No. 16/993,776, filed on Aug. 14, 2020, now Pat. No. 11,510,445, which is a continuation of application No. 16/536,139, filed on Aug. 8, 2019, now Pat. No. 10,750,801.

(60) Provisional application No. 62/716,202, filed on Aug. 8, 2018.

(51) Int. Cl.
*A41D 13/12* (2006.01)
*A61M 25/02* (2006.01)

(52) U.S. Cl.
CPC ..... *A41D 13/1281* (2013.01); *A41D 13/1245* (2013.01); *A61M 25/02* (2013.01); *A61M 2025/0206* (2013.01)

(58) Field of Classification Search
CPC ............ A41D 13/1281; A41D 13/1245; A41D 27/201; A61M 25/02; A61M 2025/206
See application file for complete search history.

(56) References Cited

U.S. PATENT DOCUMENTS

| 4,666,432 A | 5/1987 | McNeish et al. |
| 5,142,702 A | 9/1992 | Piloian |
| 5,293,840 A | 3/1994 | Wedlick |
| 5,755,698 A | 5/1998 | Kagan et al. |
| 6,477,710 B1 | 11/2002 | Ojoyeyi |

(Continued)

FOREIGN PATENT DOCUMENTS

WO 2020033739 A1 2/2020

OTHER PUBLICATIONS

International Search Report and Written Opinion of the International Searching Authority for Application No. PCT/US2019/045771 dated Oct. 15, 2019 (12 pages).

*Primary Examiner* — Tajash D Patel
(74) *Attorney, Agent, or Firm* — Frost Brown Todd LLP

(57) ABSTRACT

Medical apparatuses for securing, protecting, retaining, and/or concealing various medical devices such as catheters or electrical leads are disclosed herein. The medical apparatus can be a garment which for use by a patient having a central venous catheter in place. Medical garments as disclosed herein can be used for a wide variety of medical devices attached to a patient, by implantation or otherwise, for varying lengths of time. Medical garments described herein may be used with any of a variety of medical devices which include or comprise one or more conduits used for medical treatment or diagnosis, including conduits which comprise catheters as well as electrical conduits such as electrical leads.

20 Claims, 16 Drawing Sheets

(56) References Cited

U.S. PATENT DOCUMENTS

| | | |
|---|---|---|
| 6,647,552 B1 | 11/2003 | Hogan |
| 6,681,404 B1 | 1/2004 | Adlard et al. |
| 7,364,491 B2 | 4/2008 | Updyke |
| 8,418,267 B2 | 4/2013 | Shaw et al. |
| 10,750,801 B2 | 8/2020 | Bentley |
| 11,510,445 B2 * | 11/2022 | Bentley .............. A41D 13/1281 |
| 2009/0100569 A1 | 4/2009 | Butler |
| 2010/0042051 A1 | 2/2010 | Walker |
| 2014/0310850 A1 | 10/2014 | Hudak et al. |
| 2015/0374048 A1 | 12/2015 | Theodossiou |
| 2016/0050995 A1 | 2/2016 | Bentley et al. |
| 2017/0049166 A1 | 2/2017 | Shorter |
| 2020/0046047 A1 | 2/2020 | Bentley |

* cited by examiner

MEDICAL APPARATUS

CROSS-REFERENCE TO RELATED APPLICATIONS

The present application is a continuation of U.S. patent application Ser. No. 16/993,776, filed Aug. 14, 2020, which is a continuation of U.S. patent application Ser. No. 16/536,139, filed Aug. 8, 2019, which claims priority to U.S. Provisional Patent Application Ser. No. 62/716,202, filed Aug. 8, 2018, the disclosures of each of which are hereby incorporated by reference in their entirety.

TECHNICAL FIELD

The present disclosure relates to a medical apparatus for protecting, securing, retaining, and/or concealing various medical devices such as catheters or electrical leads.

BACKGROUND

A variety of medical devices are commonly attached to patients for extended periods of time, for a variety of reasons and in a variety of ways (e.g., adhesively, implanted, inserted into, attached via straps or other attachment members, etc.). For example, venous catheters, peritoneal catheters and pumps (such as those used for dialysis), gastric feeding tubes ("G-tubes"), various types of drainage tubes, various other types of vascular catheters, and various other medical devices are commonly implanted or otherwise attached to patients. In many such instances, a portion of the medical device (e.g., one or more conduits such as catheter tubes and/or electrical leads) extends out of or otherwise away from the patient's body. As a result, the patient often will have a portion of the medical device which must be secured in some manner, particularly when the device is not being used. If not secured in some manner, particularly if not secured close to the patient's body, a loose portion of the medical device may get in the way of normal activities or may even be inadvertently pulled or become entangled to the point that the device itself is compromised and/or the patient suffers adverse consequences (e.g., irritation, pain, inflammation, or worse). In addition, a visible exterior portion of the medical device (e.g., catheter tubing or electrical leads) may also cause embarrassment for the patient, particularly children.

BRIEF DESCRIPTION OF THE DRAWINGS

The following detailed description of embodiments of the present disclosure can be best understood when read in conjunction with the drawings enclosed herewith.

Figure 1:
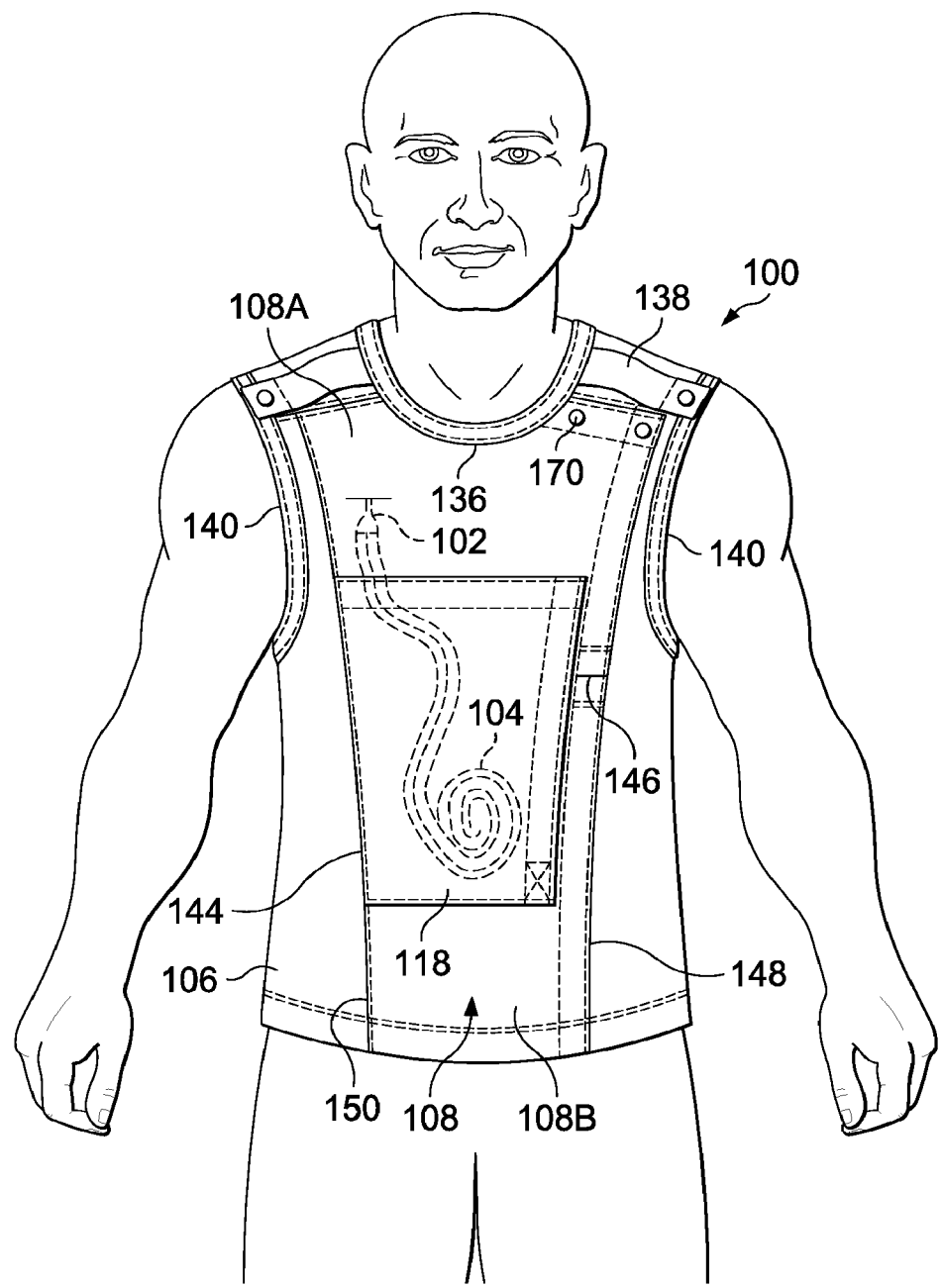
FIG. 1 is a schematic representation of an example medical apparatus according to one embodiment of the disclosure.
Figure 2:
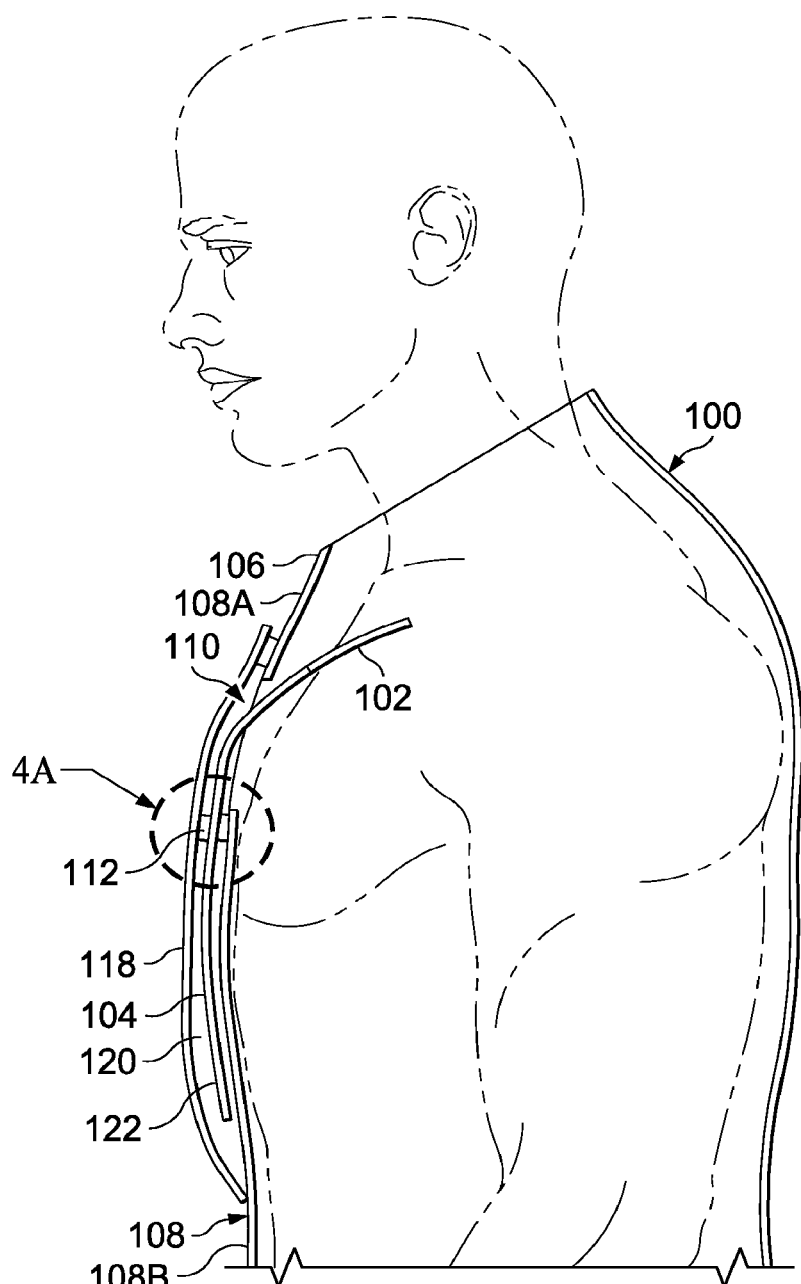
FIG. 2 is a side cross-sectional representation of a medical apparatus according to one embodiment of the disclosure.

The embodiments set forth in the drawings are illustrative in nature and not intended to be limiting. Moreover, individual features of the drawings and the disclosure will be more fully apparent and understood in view of the detailed description.

DETAILED DESCRIPTION

Certain embodiments are hereinafter described in detail in connection with the views and examples of FIGS. 1-17.

Various non-limiting embodiments of the present disclosure will now be described to provide an overall understanding of the principles of the structure, function, and use of the apparatuses, systems, methods, and processes disclosed herein. One or more examples of these non-limiting embodiments are illustrated in the accompanying drawings. Those of ordinary skill in the art will understand that systems and methods specifically described herein and illustrated in the accompanying drawings are non-limiting embodiments. The features illustrated or described in connection with one non-limiting embodiment may be combined with the features of other non-limiting embodiments. Such modifications and variations are intended to be included within the scope of the present disclosure.

Reference throughout the specification to "various embodiments," "some embodiments," "one embodiment," "some example embodiments," "one example embodiment," or "an embodiment" means that a particular feature, structure, or characteristic described in connection with any embodiment is included in at least one embodiment. Thus, appearances of the phrases "in various embodiments," "in some embodiments," "in one embodiment," "some example embodiments," "one example embodiment, or "in an embodiment" in places throughout the specification are not necessarily all referring to the same embodiment. Furthermore, the particular features, structures or characteristics may be combined in any suitable manner in one or more embodiments.

The examples discussed herein are examples only and are provided to assist in the explanation of the apparatuses, devices, systems and methods described herein. None of the features or components shown in the drawings or discussed below should be taken as mandatory for any specific implementation of any of these the apparatuses, devices, systems or methods unless specifically designated as mandatory. For ease of reading and clarity, certain components, modules, or methods may be described solely in connection with a specific FIG. Any failure to specifically describe a combination or sub-combination of components should not be understood as an indication that any combination or sub-combination is not possible. Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

The medical apparatus of the present disclosure can be a garment, and is described herein as a medical garment. However, in general, the medical apparatus need not be worn as a garment, and features disclosed herein can be beneficial to an apparatus not worn by a patient. Medical garments for protecting, retaining, and/or concealing various medical devices such as catheters or electrical leads are disclosed herein. Medical garments disclosed herein can be for use by a patient having a central venous catheter in place Medical garments as disclosed herein can be used for a wide variety of medical devices attached to a patient, by implantation or otherwise, for varying lengths of time. Medical garments described herein may be used with any of a variety of medical devices which include or comprise one or more conduits used for medical treatment or diagnosis, including conduits which comprise catheters as well as electrical conduits such as electrical leads. For example, medical garments according to embodiments disclosed herein can be adapted for use with peritoneal catheters and pumps (such as those used for dialysis), gastric feeding tubes ("G-tubes"), various types of drainage tubes, various other types of vascular catheters, electrical leads, including medical devices which include or require electrical leads (e.g., Holter monitors or portable TENS devices), airway tubes, and various other medical devices. Thus, while generally described in the context of catheters, and more specifically, central venous catheters, the present disclosure is not limited to medical garments specifically adapted for or intended to be used by patients having a central venous catheter in place.

Embodiments described herein provide a medical garment which facilitates a patient's engaging in normal daily activities while a medical device such as a central venous catheter remains attached to the patient. Garments described herein not only conceal the medical device when it is not being used (and in some cases while it is being used), but also prevent portions of the medical device becoming entangled or pulled during normal activities of the patient. Such entangling and pulling, can lead to treatment delays and interruptions and/or, they can have a serious negative impact on the patient's health and safety.

Embodiments of the medical garment described herein can include a pocket, and an access opening located within the pocket through which a portion of a medical device attached to a patient (e.g., a portion of catheter tubing and/or a component of a medical device such as electrical leads) may pass from the interior of the garment into the pocket. In some embodiments, the access opening may also be used to access the patient adjacent the garment's access opening in order to, for example, examine and/or clean a catheter exit site in the patient's skin without having to remove the garment and, in some instances, without having to open the garment (other than the pocket). In embodiments, the pocket or a portion of the pocket can be waterproof. By waterproof is meant that the waterproof portion is impervious to water. Waterproofing can be achieved, for example, by including a water impervious polymer film in the pocket. In embodiments, the pocket or a portion of the pocket can be water resistant. By water repellant is meant that the water resistant portion is able to resist the penetration of water to some degree but not entirely. In embodiments, the pocket or a portion of the pocket can be water repellant. By water repellant is meant that the water repellant portion is not easily penetrated by water, especially as a result of being treated for such a purpose with a surface coating. In embodiments the pocket can be camouflaged, that is, designed in shape, style, and/or color, to blend in with the medical garment to which it is affixed.

Some embodiments further include low profile anchor member which can be disposed within the pocket. By "low profile" is meant a restraining and securing member that is substantially flat, flexible, and relatively smooth without extending substantially outwardly from the portion of the medical apparatus to which it is affixed. In an embodiment, for example, the low profile anchor can comprise two strips of woven fabric that mate and connect as spaced apart joining locations, thereby defining securing channels between adjacent joining locations (e.g., snaps, as described herein) and the mating strips of woven fabric. In such an embodiment, the low profile anchor can be soft, flexible, and extend outwardly from the portion of the medical apparatus to which it is affixed a distance of less than about 0.75 inches, or about 0.5 inches, or about 0.25 inches, where the distance is the sum of the thickness of the two fabric strips and the outside diameter of a catheter secured in the low profile anchor. Thus, when a medical apparatus in the form of a garment is worn, the low profile anchor can be soft, flexible, and relatively flat, not protruding outwardly from the patient's body. The low profile anchor can be made partially, or entirely, of fabric, such as a woven or nonwoven fabric. The low profile anchor can be affixed to the medical apparatus in a substantially non-removable manner, such as by sewing a portion of the low profile anchor to the medical apparatus, e.g., a garment. The low profile anchor can be non-plastic, that is, not made in part or in whole of molded polymer parts, which can be bulky and obtrusive when incorporated into a garment. The low profile anchor member can be adapted to secure a portion of a medical device (e.g., catheter tubing or other conduit such as electrical leads) in order to limit movement of the secured portion. In certain embodiments, the low profile anchor member can be load bearing with respect to the portion of the medical device extending from the patient through the access opening into the pocket and can provide strain relief. The load bearing and strain relief features of the low profile anchor member help to prevent or reduce the transfer of a pulling force on the medical device to the location where the device is attached to or otherwise enters the patient. For example, when a catheter tube is retained by the low profile anchor member, the low profile anchor member (and the garment itself) will resist any pulling force applied to the catheter tube (by gravity or otherwise), thereby reducing or eliminating force applied to the catheter at the site of insertion into the patient. In other words, the low profile anchor member helps to prevent the catheter (or other medical device portion retained by the anchor) from tugging on the catheter exit wound (or other location where the medical device is attached to or enters a patient).

Some embodiments are also configured to allow the medical garment to be donned or removed by a patient (or positioned on or removed from a patient) without the need to remove or disconnect the medical device attached to the patient, even if that medical device is being used at the time. For example, embodiments allow the garment to be donned or removed by a patient having a central venous catheter extending from their chest, even while the catheter is being used to infuse medication into the patient. In general the less various tubes or wires are disconnected, the better is the care and comfort of the patient.

FIGS. 1-4 depict one embodiment of a medical garment 100, as worn by a patient who has a venous access catheter 102 in place. A catheter tube 104 from the venous access catheter 102 extends from the entry site in the patient's chest, beneath the medical garment 100. Medical garment 100 can be generally shaped and styled as any type of garment worn over at least the upper torso of a patient, including, without limitation, shirts, jerseys, smocks, vests, parkas, coats, t-shirts, blouses, and bodysuits, including infant and toddler bodysuits which cover the upper torso and at least a portion of the lower torso (sometimes referred to as a "sleeper" when portions or all of the child's legs are covered). As used herein, "upper" and "lower" are used in relation to a patient wearing a medical garment, with upper being above lower when a patient is in a standing position.

Medical garment 100 can include a body portion comprising a front panel 106 having an outward-facing surface 108, an access opening 110 extending through the front panel 106, and a low profile anchor 112 that can be attached to the front panel 106. The low profile anchor 112 can be attached to the outward-facing surface 108 beneath the access opening 110. As used herein, "beneath" means lower or below, when the garment is worn by a patient standing erect.

The medical garment 100 can also include an outer panel 118 attached to the outward-facing surface 108 of the front panel 106 such that a pocket 120 extends downwardly from a portion near low profile anchor 112. The pocket 120 can be configured to retain a distal length 122 of the catheter tube 104 that extends below the low profile anchor 112. It will be understood, however, that the pocket may be used to retain any of a variety of items, as further described herein.

Figure 3:
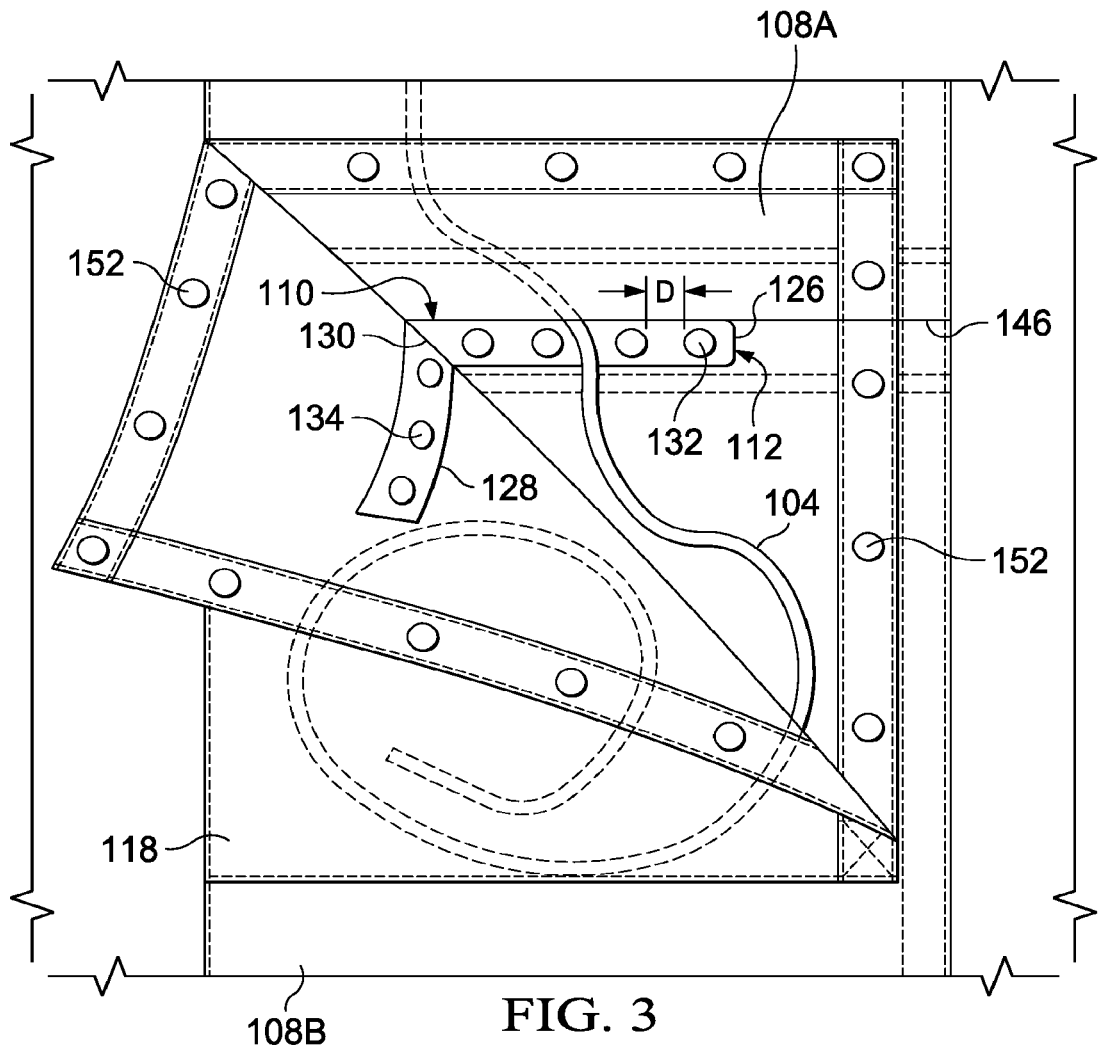
FIG. 3 is a representation of a portion of a medical apparatus according to one embodiment of the disclosure.
Figure 4:
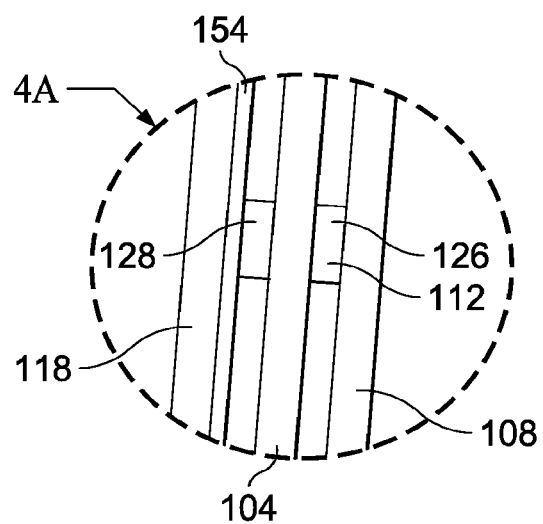
FIG. 4 is a representation of detail 4A of FIG. 2 according to one embodiment of the disclosure.

As depicted in FIGS. 3 and 4, the low profile anchor 112 in the illustrated embodiment can be adapted to receive and retain a portion of catheter tube 104. Low profile anchor 112 can include a first strip member 126 and a mating second strip member 128 that, when in a mated state with the first strip member 126 can secure the catheter tube 104, providing the above mentioned retaining and securing function. The first strip member 126 can be attached to the front panel 106 of the medical garment 100. The mating second strip member 128 can be hingedly joined to the first strip member 126 at a hinged portion 130. In another embodiment (not shown), the mating second strip member 128 can be attached to the inside surface of the outward-facing surface 108 of the front panel 106 of pocket 120. In another embodiment (not shown), the mating second strip member 128 can be a discrete member that can be joined to the first strip member 126 to secure the catheter tube 104.

The first strip member 126 and mating second strip member 128 can be joined together at discrete locations such that a catheter tube can be operationally secured between the first strip member 126, the mating second strip member 128, and the joined discrete locations. By "operationally secured" is meant that the low profile anchor 112 provides load bearing and strain relief forces to the catheter tube 104 (or other medical device) to help prevent or reduce the transfer of a pulling force on the catheter tube 104 at the location where the catheter tube 104 is attached to or otherwise enters the patient. In one embodiment, first strip member 126 can have a plurality of discrete, spaced apart first joining members 132, which can be, for example, snaps, hooks, or adhesive members. Likewise, mating second strip member 128 can have a plurality of discrete, spaced apart second joining members 134, intended to mate with corresponding spaced apart first joining members 132 such that a catheter tube 104 (or other medical device) can be held securely between adjacent joining members and the first and second strips. In an embodiment, the spaced apart first joining members 132 can be the female portion of a snap member, and the spaced apart second joining members 134 can be the male portion of a snap member. The spaced apart first joining members 132 and the spaced apart second joining members 134 can be separated by a dimension D that is a distance sufficient to allow the catheter tube 104 (or other medical device) to fit between without being overly squeezed or crushed so as to hinder operation. In an embodiment, the dimension D can be from about 0.1 inches to about 1.5 inches, and can be from about 0.25 inches to about 0.75 inches.

As can be understood with continuing reference to the embodiment illustrated in FIGS. 3 and 4, in operation a catheter tube 104 can be placed between adjacent of the spaced apart first joining members 132. The mating second strip member 128 can be brought into contact with the first strip, such as by moving about hinged portion 130, such that the spaced apart second joining members 134 mate with corresponding spaced apart first joining members 132. While assuring that the catheter tube 104 is not being unduly constricted, the spaced apart second joining members 134 can be joined to spaced apart first joining members 132 to secure the mating second strip member 128 to the first strip member 126, thereby operationally securing the catheter tube 104. As can be understood, the low profile anchor 112 provides the benefits of being relatively unobtrusive to the medical garment 100 when in use, can be soft, flexible, and relatively low profile such that a patient wearing the medical garment can, for example, lay on his or her stomach with relatively less discomfort due to a relatively larger, stiffer, and more obtrusive catheter tube connection member.

The first strip member 126 can be a strip of flexible and/or stretchable material, such as woven or nonwoven fabric, and can be attached to the medical garment 100 by adhesive, sewing, or the like attached to the outward-facing surface 108 of the medical garment 100. Likewise, the mating second strip member 128 can be a strip of flexible material, such as woven or nonwoven fabric, and can be attached to first strip member 126 at the hinged portion 130 by adhesive, sewing, or the like. As well, in an embodiment, the mating second strip member 128 can be attached to the inside surface of the outward-facing surface 108 of the front panel 106 of pocket 120 by adhesive, sewing, or the like. Thus, as can be understood, wires or tubing, such as the catheter tube 104, of different sizes can be accommodated by the flexibility of the low profile anchor 112. In addition, the spacing of the dimension D can be varied between adjacent of spaced apart first joining members 132 and the spaced apart second joining members 134, such that a plurality of varying dimensions D are available for holding and providing strain relief for correspondingly varying dimensions of wires or tubing entering or exiting the pocket 120.

Once inserted, a small length of the catheter tube 104 can remain external to the patient, extending outwardly from, for example, the patient's chest (at a variety of possible locations), adjacent the patient's clavicle, or other region of the upper torso. In the case of multi-lumen catheters, while a single tube with multiple internal lumens extends outwardly from the patient's body, the multiple lumens branch into individual tubes from an external hub assembly and connectors (e.g., luer fittings) that are typically provided at the ends of the individual tubes for connection to an infusion pump or other medical device. The external ends of the tube(s) of the central venous catheter are also typically capped in order to prevent contamination. The external hub assembly (not shown) can be disposed in the pocket 120.

Referring again to FIG. 1, the medical garment 100 can comprise a neck opening defined by a neckline 136 adapted to receive a wearer's (e.g., a patient's) neck there through, as well as right and left arm openings 140 adapted to receive a wearer's arms there through. Neckline 136 and right and left arm openings 140 may be formed in a variety of ways, such as by affixing (e.g., by stitching) binding strips to the garment panels, as shown. The bottom end 142 of the medical garment 100 may be finished with a stitched hem, as shown, or in other ways known to those skilled in the art. It should also be pointed out that for purposes of clarity, the various stitching used to attach the fabric panels and form various hems and other conventional garment reinforcing structures (e.g., hems) is not depicted, but can be achieved by methods and devices known in the art. The neckline 136 of the medical garment 100 can be sized for varying neck sizes, including for children, adolescents, and adults. In an embodiment, the neckline 136 can be a V-neck design.

Figure 5:
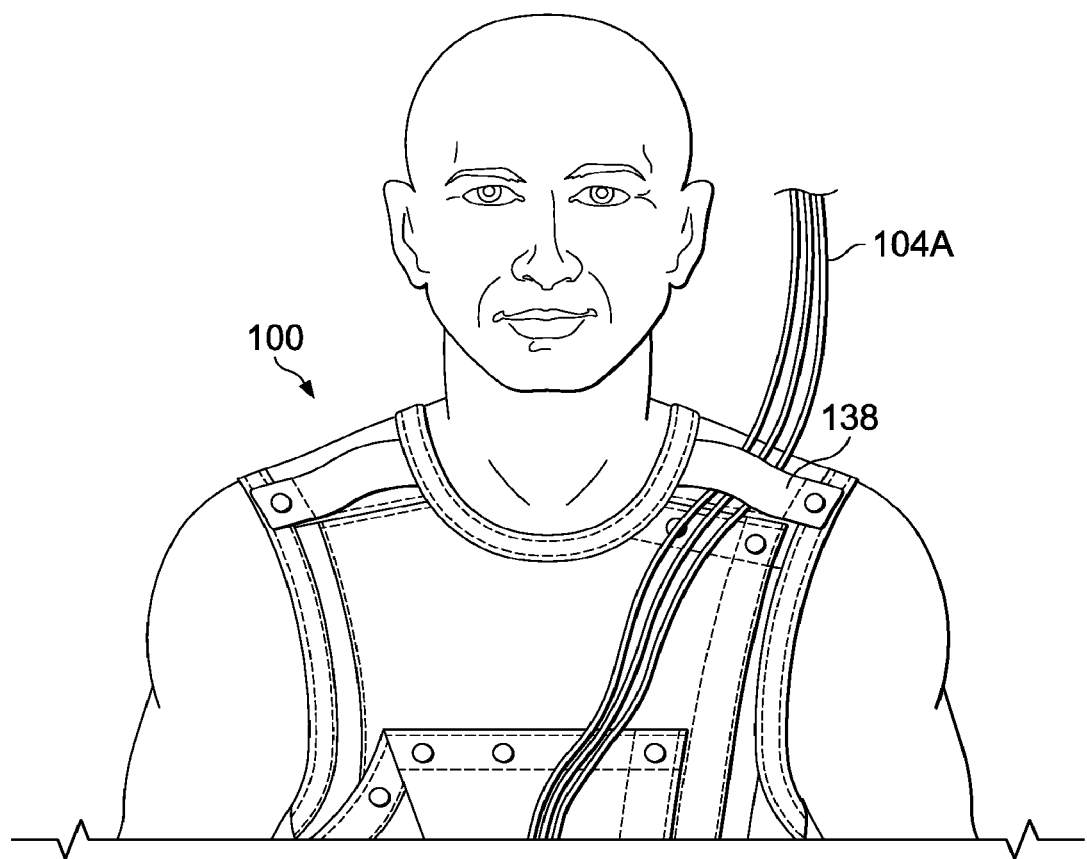
FIG. 5 is a representation of a portion of a medical apparatus according to one embodiment of the disclosure.

A shoulder strap 138 can be disposed on one or both shoulder portions of the medical garment 100 as shown in FIG. 1, and in use in FIG. 5. The shoulder strap 138 can be a flexible flap of material releasably engageable to securely hold a portion of wires or tubing, including the catheter tube 104 on the shoulder portion of the medical garment 100. As shown in FIG. 5, the shoulder strap 138 can secure in place on the medical garment 100 multiple catheter tubes 104A, wires, or other medical devices, including, for example, multiple tubes connected to the aforementioned external hub assembly residing in the pocket 120 of the medical garment 100.

With continuing reference to FIGS. 1-4, the outward-facing surface 108 of the example medical garment can comprise two discrete panels, an upper panel 108A and a lower panel 108B, both attached to the front panel 106, and separately openable, for example about a seam 144 at which both the upper panel 108A and the lower panel 108B are attached to the front panel 106. The upper panel 108A and the lower panel 108B can be generally rectangular shaped with peripheral edges defining the shape. The upper panel 108A and the lower panel 108B can be juxtaposed to one another. By juxtaposed, as used herein, is meant that adjacent panels can be in close proximity, i.e., in a closely spaced arrangement. For example, as disclosed herein with respect to upper, lower, (and, central, as disclosed below) panels, being juxtaposed means that at least one of a panel's peripheral edges is in close proximity, including being overlapping with, a peripheral edge of an adjacent panel. By being juxtaposed one to another, adjacent panels define an access opening, that is, an opening providing access from the outward facing surface of the body portion to an inward facing surface. Thus, the upper panel 108A and the lower panel 108B can be separated one from the other at an access opening 146 extending at least partially from a left edge 148 to a right edge 150 (left and right with respect to the wearer). The access opening 146 permits the upper panel 108A or the lower panel 108B to be opened independently with respect to one another. Further, the access opening 146 can have a gap width of between about 0 inches to about 3 inches, and a portion of the access opening 146 can be an access opening through which a catheter tube 104 transverses from the outside of the garment to the wearer's body. Each of the upper panel 108A and the lower panel 108B can be secured in a closed position (as shown in FIG. 1) by any known method, including be mating panel snap members, hook and loop fasteners, and the like. In use, the upper panel 108A can be opened independently of the lower panel 108B to access wounds accessible on the patient without removing the medical garment 100, for example, by disconnecting and connecting a connecting member, such as one or more snapping members 170. Likewise, the lower panel 108B can be opened independently of the upper panel 108A to access wounds accessible on the patient without removing the medical garment 100. In an embodiment, it may be necessary to first open the outer panel 118 prior to opening one or both of the upper panel 108A and the lower panel 108B.

The outer panel 118 can span and be attached in locations on both the upper panel 108A and the lower panel 108B, as depicted in FIGS. 1 and 3. The outer panel 118 can have a shape, such as a rectangle, having peripheral edges, with a first peripheral edge being attached to the body portion by a seam, and at least one of the remaining peripheral edges being affixed to the body portion by a plurality of spaced apart joining members, such as mating pocket flap snap members 152. Mating pocket flap snap members 152 can secure the outer panel 118 in a closed position, as depicted in FIG. 1, and can be opened by selectively opening one or more of the mating pocket flap snap members 152 for access into pocket 120. The mating pocket flap snap members 152 can be disposed in a spaced-apart configuration such that a catheter tube 104, or other medical device, can be routed out of the pocket 120. The number and placement of the mating pocket flap snap members 152 can be predetermined based on the type and number of medical devices intended to be utilized, as well as ease of access to, and secure closure of, the pocket 120. The pocket 120 can be water-resistant or water-proof. The pocket 120 can have a water-resistant liner 154 that at least partially covers the entire pocket surface. In an embodiment the water-resistant liner 154 can be joined to an inner surface of the pocket 120. In an embodiment the water-resistant liner 154 can be joined to an outer surface of the pocket 120.

In an embodiment, outer panel 118 can be attached in locations on only one or both of the upper panel 108A and lower panel 108B. For example, an outer panel 118 disposed on only the lower panel 108B could be used to accommodate G or J tubing.

For embodiments disclosed herein, the medical garment 100, or portions thereof, can be made of any material, including woven and nonwoven fabrics. The material can be flexible, stretchable, and soft. The material used can include rayon, including rayon derived from bamboo and cotton. Bamboo can provide anti-microbial benefits. In an embodiment, the material can be at least 50% bamboo fibers, or at least 75% bamboo fibers, or at least 90% bamboo fibers, or 100% bamboo fibers.

Figure 6:
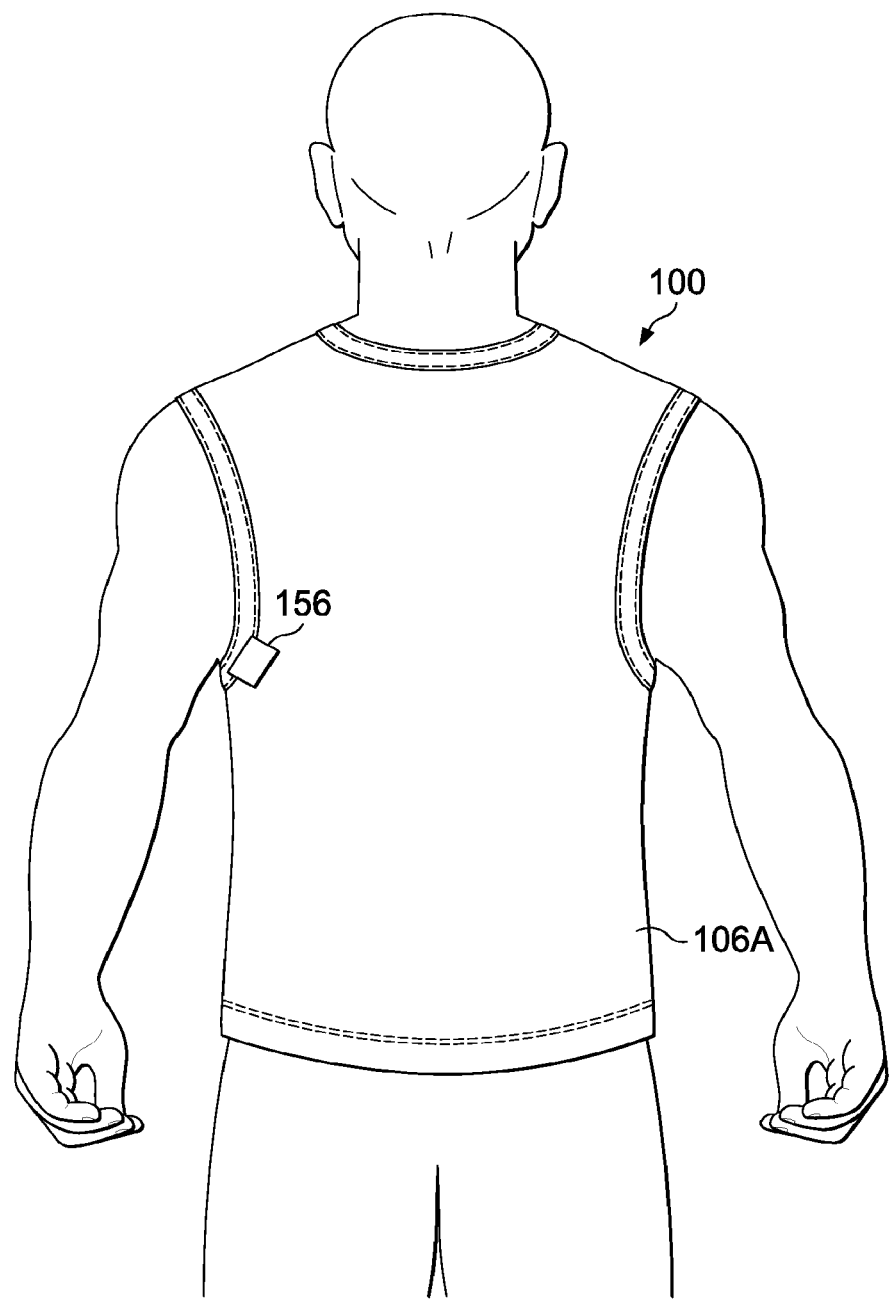
FIG. 6 is a rear-view of a medical apparatus according to one embodiment of the disclosure.

Referring now to FIG. 6, there is shown a view of the back panel 106A of the medical garment 100 being worn by a patient. The back panel 106A can be a relatively soft, flexible material of woven or nonwoven fibers. The back panel 106A can be a unitary, one-piece panel joined to the front panel 106 at the sides and top. The back panel 106A can also be multi-piece, and can have openings and removable panels, as described on the front panel 106 herein. As shown in FIG. 6, another feature that can be implemented on embodiments of the medical garment 100 with some or all of the features described herein is a sensor 156 that can be in wired or wireless communication with an electronic device to which data from the sensor 156 can be transmitted.

Wireless technology, such as Bluetooth® can be utilized to transmit data to a remote device, such as a mobile computer, smartphone, system server, or the like. In an embodiment, the sensor 156 can be located in close proximity to a portion of the patient's body from which data is desired to be gathered. For example, in an embodiment a sensor 156 can be joined to the medical garment 100 on a portion that, when worn, resides under a patients arm, that is, in or near the armpit, as shown in FIG. 6. For example, a sensor 156 can monitor cholesterol, blood sugar levels, temperature, blood pressure, and/or heart rhythms. In an embodiment, the sensor can include any of known sensors for detecting and transmitting bio-data, together with electronics configured to detect and transmit data desired to be collected and transmitted.

In an embodiment, the sensor 156 can be used to detect other patient-centric data. For example, the sensor 156 can be of a type that can detect a fall, including the timing and the severity of a fall, and/or the length of time since a fall, between falls, and the like. In an embodiment, the sensor can include an accelerometer or other force sensor suitable for detecting falls, together with electronics configured to detect and transmit data desired to be collected and transmitted.

Figure 7:
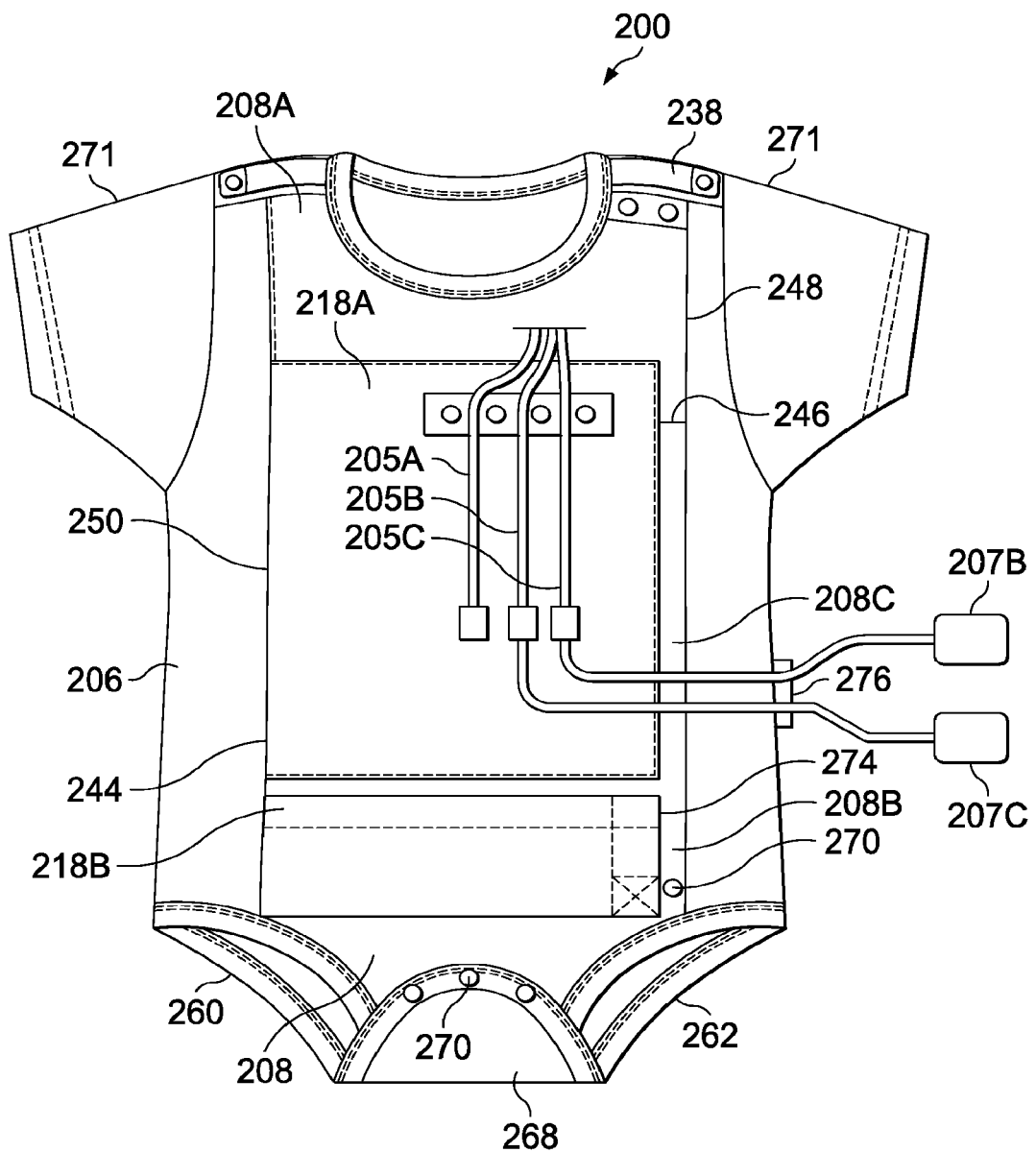
FIG. 7 is a representation of a medical apparatus according to one embodiment of the disclosure.
Figure 8:
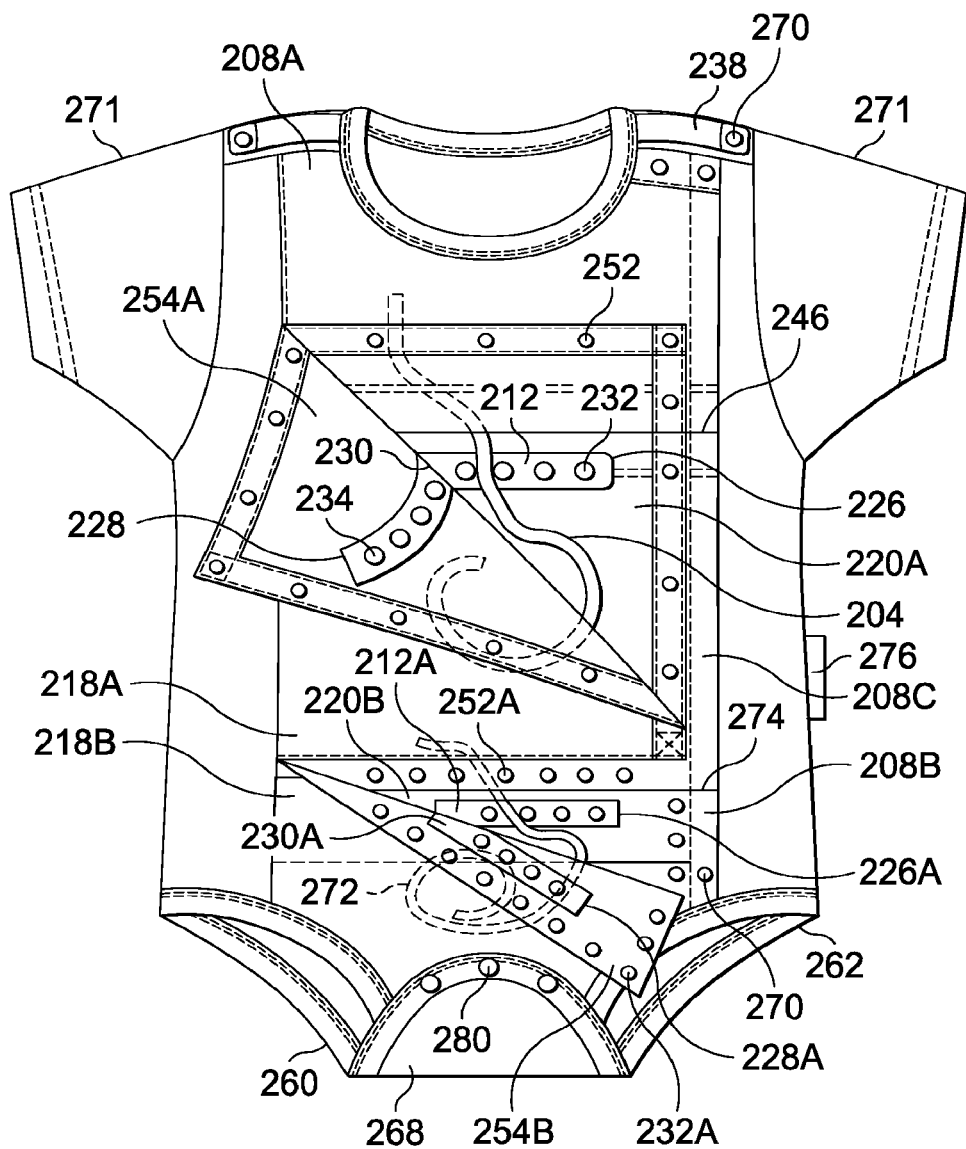
FIG. 8 is a representation of a medical apparatus according to one embodiment of the disclosure.

Referring now to FIGS. 7 and 8, there is shown an embodiment of a medical garment 200 that can have, in addition to the disclosed features, some or all the other features described herein. Instead of being configured as a shirt, as shown in FIG. 1, medical garment 200 can be configured as an infant or toddler bodysuit which covers at least a portion of the upper torso and at least a portion of the lower torso. In the embodiment shown in FIGS. 7-8, the medical garment 200 can be configured such that a right leg cuff 260 and left leg cuff 262 encircle an infant's legs adjacent the crotch area such that the garment has no pant legs. The center flap 268 can be arranged to extend over the buttocks area of an infant and over a portion of the front crotch area over a part of the lower portion of front panel 206. Center flap snaps 280 (or other suitable fasteners) can be provided on center flap 268 and can be arranged to mate with, and fasten to, corresponding snaps (not shown) on the lower portion of front panel 206. Further, as discussed above, medical garment 200 can include a shoulder strap 238 on one or both shoulder portions of the medical garment 200. Further, the medical garment 200 can have a sleeve 271, which can be a long or short sleeve, as is known in infant or toddler bodysuits.

The outward-facing surface 208 of the example medical garment 200 can comprise three discrete panels, an upper panel 208A and a lower panel 208B as well as a central panel 208C, each being attached to the front panel 206, and separately openable, for example about a seam 244 at which each of the upper panel 208A, the lower panel 208B, and central panel 208C can be attached to the front panel 106. As discussed herein, the upper panel 208A, the lower panel 208B, and the central panel 208C can each be generally rectangular shaped with peripheral edges defining the shape. The upper panel 208A and the central panel 208C can be juxtaposed to one another, as discussed above, to define an upper access opening 246. Likewise, the central panel 208C and the lower panel 208B can be juxtaposed to one another, as discussed above, to define a lower access opening 274. Thus, the upper panel 208A and the central panel 208C can be separated one from the other at the upper access opening 246, which can extend at least partially from a left edge 248 to a right edge 250 (left and right with respect to the wearer). The upper access opening 246 permits the upper panel 208A or the central panel 208C to be opened independently with respect to one another. Further, the upper access opening 246 can have a gap width of between about 0 inches to about 3 inches, and a portion of the upper access opening 246 can be an access opening through which a catheter tube 204 transverses from the outside of the garment to the wearer's body. Each of the upper panel 208A and the central panel 208C can be secured in a closed position (as shown in FIG. 7) by any known method, including by mating panel snapping members 270, hook and loop fasteners, and the like. In use, the upper panel 108A can be opened independently of either the central panel 208C or lower panel 208B to access wounds accessible on the patient without removing the medical garment 100.

Likewise, the lower panel 208B and the central panel 208C can be separated one from the other at the lower access opening 274, which can extend at least partially from a left edge 248 to a right edge 250 (left and right with respect to the wearer). The lower access opening 274 permits the lower panel 208B or the central panel 208C to be opened independently with respect to one another. Further, the lower access opening 274 can have a gap width of between about 0 inches to about 3 inches, and a portion of the lower access opening 274 can be an access opening through which a medical device, such as a G-tube 272 (or J-tube, or the like) transverses from the outside of the garment to the wearer's body. Each of the lower panel 208B and the central panel 208C can be secured in a closed position (as shown in FIG. 7) by any known method, including be mating panel snapping members 270, hook and loop fasteners, and the like. In use, the lower panel 208B can be opened independently of either the central panel 208C or the upper panel 208A to access wounds accessible on the patient without removing the medical garment 100.

As discussed above with respect to outer panel 118, an upper outer panel 218A can span at least a portion of the upper access opening and can be attached in locations on both the upper panel 208A and the central panel 208C, as depicted in FIGS. 7 and 8. The upper outer panel 218A can have a shape, such as a rectangle, having peripheral edges, with a first peripheral edge being attached to the body portion by a seam, and at least one of the remaining peripheral edges being affixed to the body portion by a plurality of spaced apart joining members, such as mating upper pocket flap snap members 252A. Mating upper pocket flap snap members 252A (or other connection method, such as hook and loop fastener) can secure the upper outer panel 218A in a closed position, as depicted in FIG. 7, and can be opened by selectively opening one or more of the mating upper pocket flap snap members 252A for access into an upper pocket 220A. The mating upper pocket flap snap members 252A can be disposed in a spaced-apart configuration such that a catheter tube 204, or other medical device, can be routed out of the upper pocket 220A, and through the upper access opening to the upper torso of the patient. The number and placement of the mating upper pocket flap snap members 252A can be predetermined based on the type and number of medical devices intended to be utilized, as well as ease of access to, and secure closure of, the upper pocket 220A. The upper pocket 220A can be water-resistant or waterproof. The upper pocket 220A can have an upper water-resistant liner 254A that at least partially covers the entirety of the upper pocket 220A surface, either inside as depicted in FIG. 8, or outside, or both. In an embodiment the upper water-resistant liner 254A can be joined to an inner surface of the upper pocket 220A. In an embodiment the upper water-resistant liner 254A can be joined to an outer surface of the upper pocket 220A.

Continuing to refer to FIGS. 7 and 8, a lower outer panel 218B can span and be attached in locations on both the lower panel 208B and the central panel 208C, as depicted in FIGS. 7 and 8. The lower outer panel 218B can have a shape, such as a rectangle, having peripheral edges, with a first peripheral edge being attached to the body portion by a seam, and at least one of the remaining peripheral edges being affixed to the body portion by a plurality of spaced apart joining members, such as mating lower pocket flap snap members 252B. Mating lower pocket flap snap members 252B (or other connection method, such as hook and loop fastener) can secure the lower outer panel 218B in a closed position, as depicted in FIG. 7, and can be opened by selectively opening one or more of the mating lower pocket flap snap members 252B for access into a lower pocket 220B. The mating lower pocket flap snap members 252B can be disposed in a spaced-apart configuration such that a medical tube, such as G-tube 272, or other medical device, can be routed out of the lower pocket 220B. The number and placement of the mating lower pocket flap snap members 252B can be predetermined based on the type and number of medical devices intended to be utilized, as well as ease of access to, and secure closure of, the lower pocket 220B. As shown, the lower pocket 220B can hold a length of a medical device, such as G-tube 272, as well as other medical devices for which access through the lower access opening 274 is desired or required. For example, the lower pocket 220B can hold or provide access to an ostomy device or a stoma. The lower pocket 220B can be water-resistant or waterproof. The lower pocket 220B can have a lower water-resistant liner 254B that at least partially covers the entirety of the lower pocket 220B surface, either inside as depicted in FIG. 8, or outside, or both. In an embodiment the lower water-resistant liner 254B can be joined to an inner surface of the lower pocket 220B. In an embodiment the lower water-resistant liner 254B can be joined to an outer surface of the lower pocket 220B. Because ostomy bags can leak, a waterproof pocket, e.g., lower pocket 220B, can secure an ostomy bag snug to the body, containing any leaks. Further, the lower pocket 220B can hold an ostomy pouch securely to the body and can be positioned to further hold the stoma to create a fit that can eliminate gaps between the wafer, i.e., the gasket-like medical device, and the stoma to further minimize or prevent leakage. The wafer material can be formulated to absorb moisture on the skin to minimize irritation providing greater wearing comfort and for extended wearing.

Further, as with the low profile anchor 112 described above, the medical garment 200 can have an upper low profile anchor 212 and a lower low profile anchor 212A. As discussed above, each of the upper low profile anchor 212 and a lower low profile anchor 212A can be adapted to receive and retain a portion of a medical device, such as the catheter tube 204 204 or the G-tube 272, to provide all the above-mentioned benefits, including retaining and strain relief. The upper low profile anchor 212 can include an upper first strip member 226 and a mating upper second strip member 228 that, when in a mated state with the upper first strip member 226 can secure, for example, the catheter tube 204, providing the above mentioned retaining and securing function. The upper first strip member 226 can be attached to the front panel 206, for example on the central panel 208C, of the medical garment 200. The mating upper second strip member 228 can be hingedly joined to the upper first strip member 226 at a hinged portion 230. In another embodiment (not shown), the mating upper second strip member 228 can be attached to the inside surface of the outward-facing surface 208 of the upper panel 208A of the pocket 220. In another embodiment (not shown), the mating upper second strip member 228 can be a discrete member that can be joined to the upper first strip member 226 to secure the catheter tube 204.

Likewise, the lower low profile anchor 212A can include a lower first strip member 226A and a mating lower second strip member 228A that, when in a mated state with the lower first strip member 226A can secure, for example, the G-tube 272, providing the above mentioned retaining and securing function. The lower first strip member 226A can be attached to the lower panel 208B of the medical garment 200. The mating lower second strip member 228A can be hingedly joined to the lower first strip member 226A at a hinged portion 230A. In another embodiment (not shown), the mating lower second strip member 228A can be attached to the inside surface of the lower pocket 220B. In another embodiment (not shown), the mating lower second strip member 228A can be a discrete member that can be joined to the lower first strip member 226A to secure the G-tube 272.

As can be understood from the discussion above with respect to securing the catheter tube 204, the lower first strip member 226A and mating lower second strip member 228A can have discrete spaced apart joining locations such that they can be releasably joined together at discrete spaced apart joining locations. A wire or tube, such as the G-tube 272, can be operationally secured between the lower first strip member 226A, the lower second strip member 228B, and between the joined discrete spaced apart joining locations. By "operationally secured" is meant that the lower low profile anchor 212A provides load bearing and strain relief forces to, for example, a G-tube 272, or other medical device to help prevent or reduce the transfer of a pulling force on the G-tube 272 at the location where the G-tube 272 is attached to or otherwise enters the patient. In one embodiment, the lower first strip member 226A can have a plurality of discrete, spaced apart lower joining members 232A, which can be, for example, snaps, hooks, or adhesive members, and which can be mating male and female snaps. The spaced apart lower joining members 232A can be separated by a second dimension DA (not shown) corresponding to the above-described dimension D that is a distance sufficient to allow the G-tube 272 (or other medical device) to fit between without being overly squeezed or crushed so as to hinder operation. In an embodiment, the dimension D can be from about 0.1 inches to about 1.5 inches, and can be from about 0.25 inches to about 0.75 inches.

In an embodiment, any or all of the spaced apart first joining members 132, upper joining members 232, spaced apart lower joining members 232A, and/or associated joining portions, can have visual indications communicating information relating to the type of medical devices being restrained therein. Taking the spaced apart lower joining members 232A as an example, the individual snaps, or portions of the corresponding strips, can be color-coded to communicate the type of tube being restrained, e.g., a J-tube or a G-tube, or both. Thus, a care giver opening the lower pocket 220B can determine by visual inspection which tube is which, based on the visual indications communicated by, for example, color coding. Other visual indications can be used, such as textual indicia, snap spacing (e.g., snap spacing allowing only one size tube for proper placement), and the like.

Figure 9:
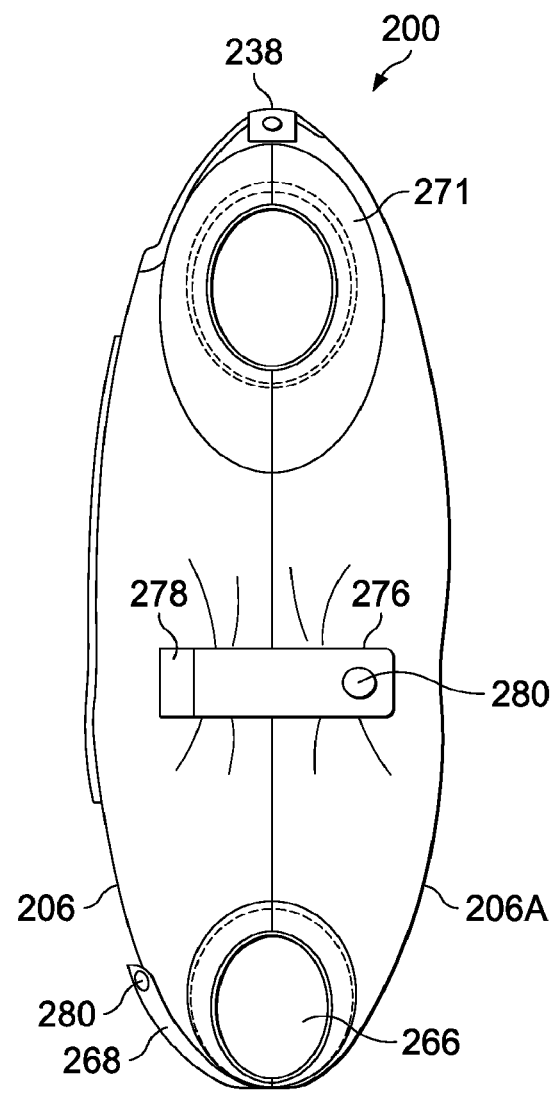
FIG. 9 is a side view of a medical apparatus according to one embodiment of the disclosure.

As seen in FIGS. 7-9, medical garment can further include a side retention strap 276. Side retention strap 276 can be constructed similar to a shoulder strap 238, and thus can comprise a strip of elastic fabric that is affixed at a proximal end 278 to a side of medical garment 200, while the distal end can be secured by one or more center flap snaps 280 provided on the side of the medical garment 200. Thus, the snap end of the side retention strap can be selectively detachable from the side of the medical garment 200 so that the side retention strap 276 can be used to retain medical devices, such as catheter tubing, against the wearer's side in a similar manner that a shoulder strap 238 may be used to retain catheter tubing and the like over a wearer's shoulder. Side retention strap 276 thus not only maintains the catheter tubing (or other conduit) out of the way, it also makes it difficult for an infant or toddler to grab and pull the tubing. Thus, side retention strap 276 can be a fabric strip hingedly sewn to the material of the medical garment 200 at a proximal end 278. The side retention strap 276 can have a length less than the distance on the medical garment 200 between the proximal end 278 and the snap connection, so that the side retention strap 276 can be used to gather excess material of the medical garment 200 to provide a closer fit on a patient. In an embodiment side retention strap 276 can have a plurality of spaced-apart snaps designed as depicted above with respect to the low profile anchor 112, and for the same purpose. By being disposed on a side of the medical garment 200 between a leg opening 266 and an arm opening, or sleeve 271 (as shown in FIG. 9), the side retention strap 276 provides for more comfortable routing of medical devices by removing them from being routed across a patient's back or front, as may be the case.

Continuing to refer to FIG. 7, and to further show the benefits of the features described herein, there is shown schematically the path of a catheter tube 204 (CVC) connected to a plurality of lumens, including a first lumen 205A, a second lumen 205B and a third lumen 205C, each of which can be secured in the upper low profile anchor 212 and secured inside the upper outer panel 218A and inside the upper pocket 220A. Further, a single lumen catheter can be accommodated, e.g., secured by looping around snap restraint of either the upper low profile anchor 212, or one on the upper outer panel 218A. Any lumens connected to external medical devices, such as the second lumen 205B and third lumen 205C, which can be connected to a first medical device 207B and second medical device 207C, respectively, as shown in FIG. 7, can be routed out of the upper pocket 220A, such as through a side seam or a slit, if provided, and routed to and secured by the side retention strap 276. Thus, as can be understood, the medical garments disclosed herein can secure and conceal tubes and wires connected to external medical devices (or they can be contained, unconnected, in a pocket, such as first lumen 205A in upper pocket 220A in FIG. 7). Further, any manipulation of medical devices and/or the medical garment can be achieved without disconnecting the connected wires or tubes.

Figure 10:
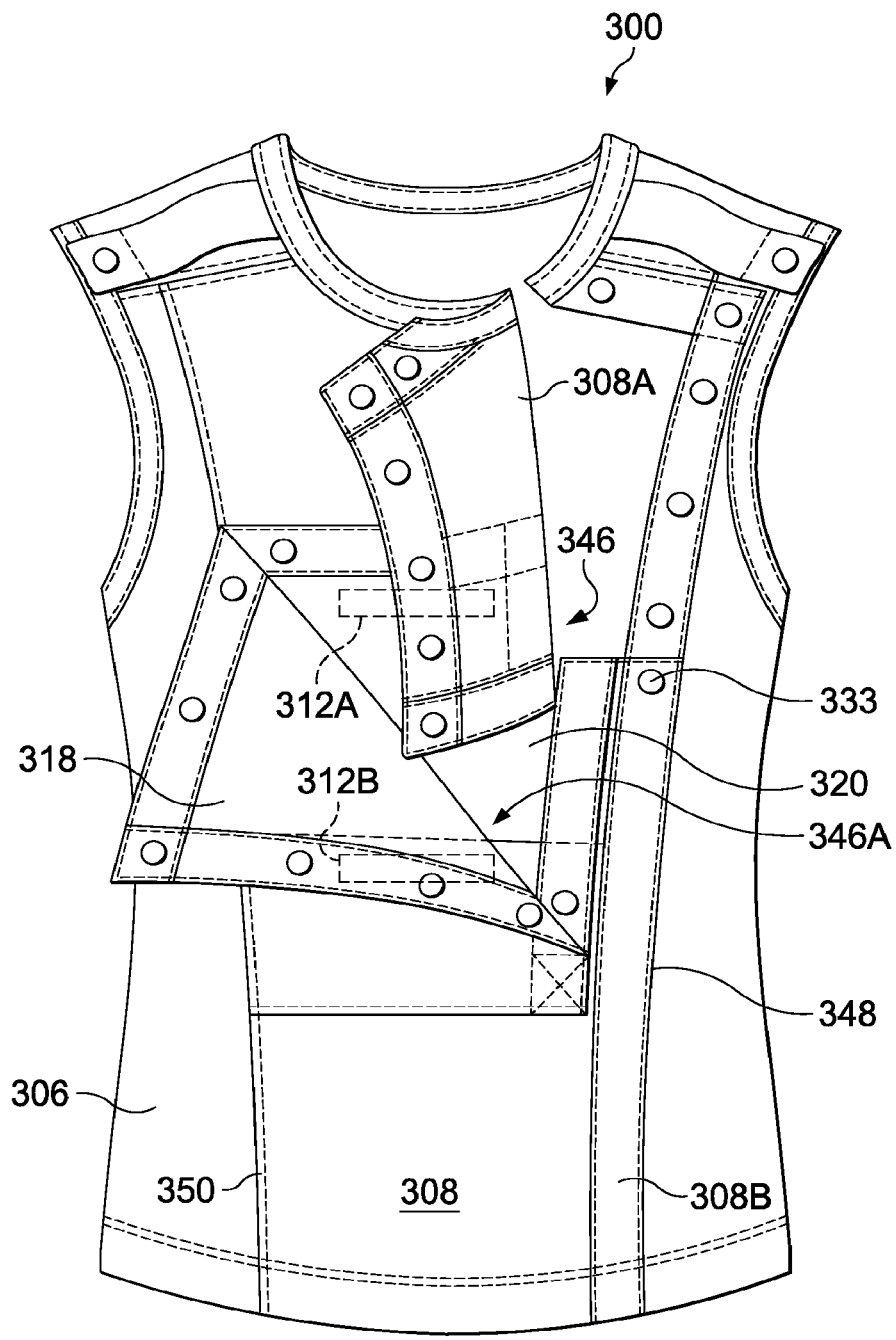
FIG. 10 is a representation of a medical apparatus according to one embodiment of the disclosure.

Referring now to FIG. 10, there is depicted a medical garment 300 that is similar in common respects to the above-described medical garments. Medical garment 300 can have some or all of the features described herein for medical garments, but which for conciseness will not be repeated for medical garment 300, which is shown to illustrate several useful features of medical garments herein and which can be used by patients, including infants, children, adolescents, adults and geriatric patients as well as their caregivers. For example, medical garment 300 can include one or both of an upper panel 308A and a lower panel 308B attached to attached to the front panel 306.

Further, an outer panel 318 attached to one or both of the upper panel 308A or the lower panel 308B can define a pocket 320 extending downwardly from a portion near an upper low profile anchor 312A (as described for low profile anchor 112 above). As discussed above, the pocket 320 can be configured to retain a distal length of medical devices, such as a catheter tube that extends below the low profile anchor 312 (not shown, but can be the same as described for low profile anchor 112 above).

As discussed above, the upper panel 308A and the lower panel 308B can be separated one from the other at an access opening 346 extending at least partially from a left edge 348 to a right edge 350 (left and right with respect to the wearer). The access opening 346 permits the upper panel 308A or the lower panel 308B to be opened independently with respect to one another. In the illustrated embodiment, the access opening 346 is formed between overlapping portions of the upper panel 308A and the lower panel 308B. In an embodiment, the upper panel 308A and the lower panel 308B are not affixed directly to one another (other than, perhaps, their far right edges along the seam connecting the right side panel, outer panel and front panels). In the illustrated embodiment, the upper panel 308A and the lower panel 308B overlap one another such that the lower edge of upper panel 308A is located below the upper edge of lower panel 308B (when the panels are closed), with the access opening 346 provided between the overlapping portions of the upper and lower front panels. In some embodiments, the overlap can be about 2 inches or less, in other embodiments about 1 inch or less, and in still further embodiments about 0.5 inches or less. Additional and various connection members, e.g., snaps, can be provided as necessary and indicated in FIG. 10, e.g., snap 333, for closure of the upper panel 308A and the lower panel 308B. It is also contemplated that the lower edge of the upper front panel and the upper edge of the lower front panel may overlap, with the access opening provided there between, such as depicted in FIG. 10.

Continuing to refer to FIG. 10, further features and benefits are described. The medical garment 300 can be utilized for patients needing to manage medical devices such as pumps. For example, patients with type 2 diabetes need to take insulin to manage their blood sugar levels. One option for such patients is to use an insulin pump. An insulin pump is a small computerized device that delivers insulin through a relatively thin tube that goes into and under a patient's skin to release insulin. Further by example, cancer patients can use chemotherapy bags and pumps, which must be kept in close proximity to the patient when being used. The medical garment 300 shown can, in addition to or instead of the catheter managing benefits described above, have additional features for patients utilizing pumps, bags, or other medical devices. Pocket 320 can be water resistant or water proof, as described above. Further, in addition to access opening 346, which can be used as described above, including for providing access for catheters to the upper chest area of a patient, a second access opening 346A can be provided at a lower portion of the medical garment 300 for access to a relatively lower portion of the patient, for example, the lower abdomen area. A second access opening can be near a lower low profile anchor 312B, which can be as described above for low profile anchor 112. In an embodiment, an insulin pump (not shown) can be received and held in the pocket 320, and an insulin delivery tube can be routed to the patient's body through the second access opening 346A and secured in the lower low profile anchor 312B. Likewise, pocket 320 can receive and hold medical devices associated with cancer treatment, such as a chemotherapy bag and a chemo pump that pumps chemotherapy chemicals through the second access opening 346A to the patient's body, with any associated tubing being routed through the second access opening 346A and secured in the lower low profile anchor 312B.

Continuing to refer to FIG. 10, further features and benefits are described. The medical garment 300 can have features making it beneficial for utilization by neonatal, e.g., NICU, patients. For example, the second access opening 346A of the medical garment 300 shown can provide, in addition to, or instead of, the catheter managing benefits described above, additional features for neonatal patients utilizing pumps, bags, or other medical devices. Specifically, an umbilical catheter can be routed through either the access opening 346 or the second access opening 346A. The umbilical catheter can be routed through the second access opening 346A and can be secured in the lower low profile anchor 312B. In an embodiment, reinforced seams, such as seams comprising LYCRA® fibers, of the medical garment 300 can at least partially surround and securely hold an umbilical catheter. In an embodiment, the medical garment can protect the umbilical by, for example, securing the umbilical feeding tube to prevent or minimize movement.

Figure 11:
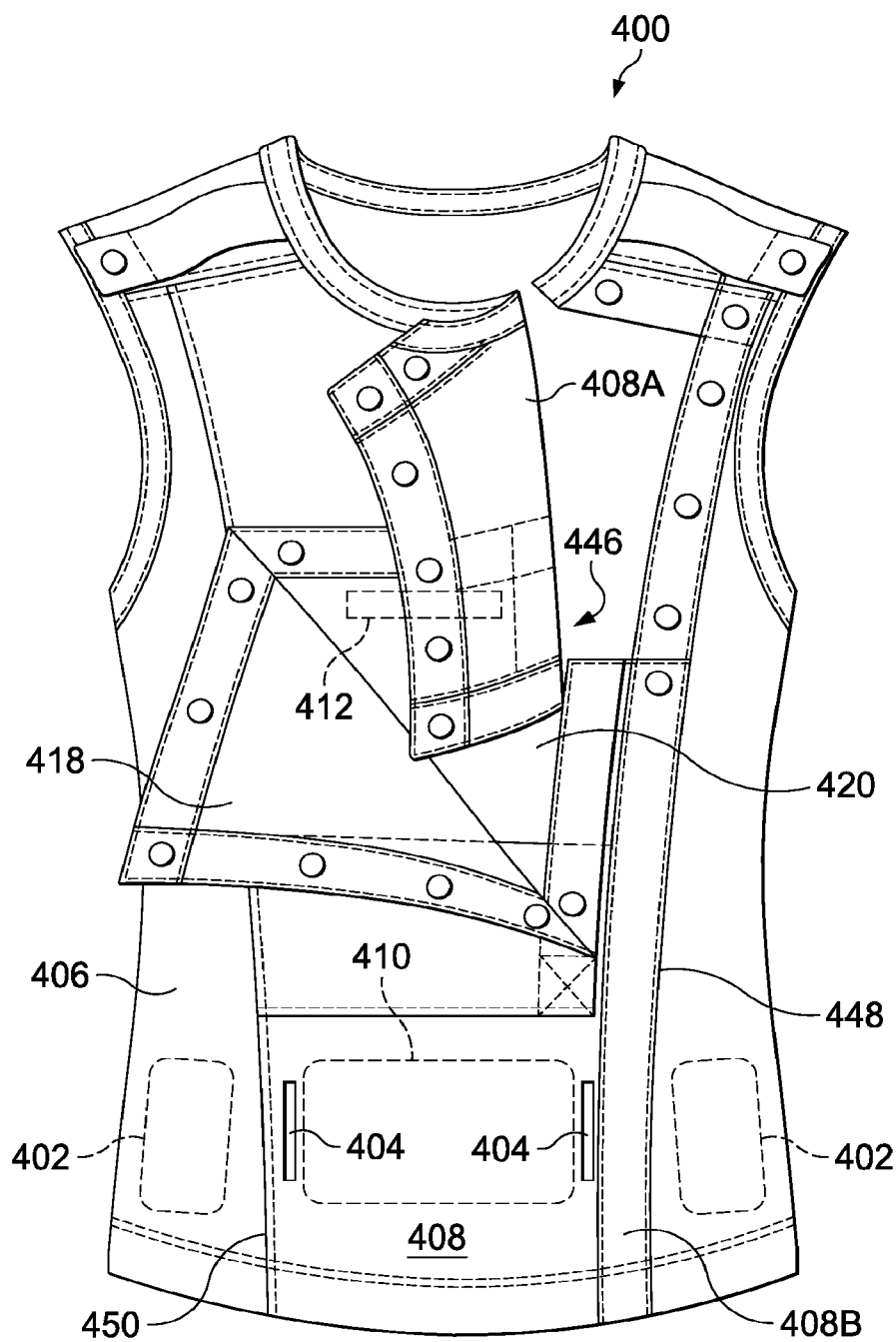
FIG. 11 is a representation of a medical apparatus according to one embodiment of the disclosure.

Referring now to FIG. 11, there is depicted a medical garment 400 that is similar in common respects to the above-described medical garments. Medical garment 400 can have some or all of the features described herein for medical garments, but which for conciseness will not be repeated for medical garment 400, which is shown to illustrate several useful features of medical garments herein and which can be used by patients, including infants, children, adolescents, adults and geriatric patients as well as their caregivers. For example, medical garment 400 can include one or both of an upper panel 408A and a lower panel 408B attached to attached to the front panel 406. Further, an outer panel 418 attached to one or both of the upper panel 408A or the lower panel 408B can define a pocket 420 extending downwardly from a portion near a low profile anchor 412 (as described for low profile anchor 112 above). As discussed above, the pocket 420 can be configured to retain a distal length of medical devices, such as a catheter tube that extends below the low profile anchor.

The medical garment 400 shown in FIG. 11 can be useful for patients requiring the use of a left ventricular assist device (LVAD) or a right ventricular assist device (RVAD), which can involve the surgical implantation of a battery-operated, mechanical pump, which then helps the left (or right) ventricle main pumping chamber of heart pump blood to rest of body. Thus, the medical garment can have features that aid in the securing of various medical devices associated with LVAD or RVAD, including being made of a breathable, compression fitting fabric that can "hug" the body in order to relatively discretely secure the cables, accommodate the drive line. Other features can be utilized to protect the computer, and contain and secure batteries in place. For example, at least one, and in an embodiment two, first auxiliary pocket(s) 402 can be provided, for example at the lower side portions as depicted in FIG. 11. The first auxiliary pocket(s) can contain and secure an electronic device, such as a computer, necessary for the operation of the LVAD OR RVAD. The first auxiliary pocket(s) can comprise various slits and openings for drive lines and other cables. For example, a slit 404 interiorly situated in the first auxiliary pocket 402 and extending to a second auxiliary pocket 410, which can be generally adjacent the wearer's abdomen and can also be used to enclose and contain components such as a computer, pump, cables, tubes, and the like. Both the first auxiliary pocket(s) 402 and the second auxiliary pocket 410 can have closure mechanisms, including snaps, hooks, hook and loop fasteners, and the like, on any suitable edge or edges, including, for example, the outside edges and/or the top edge. A specially designed hook and eyes strap can secure a battery under each arm within a waterproof pocket.

Figure 12:
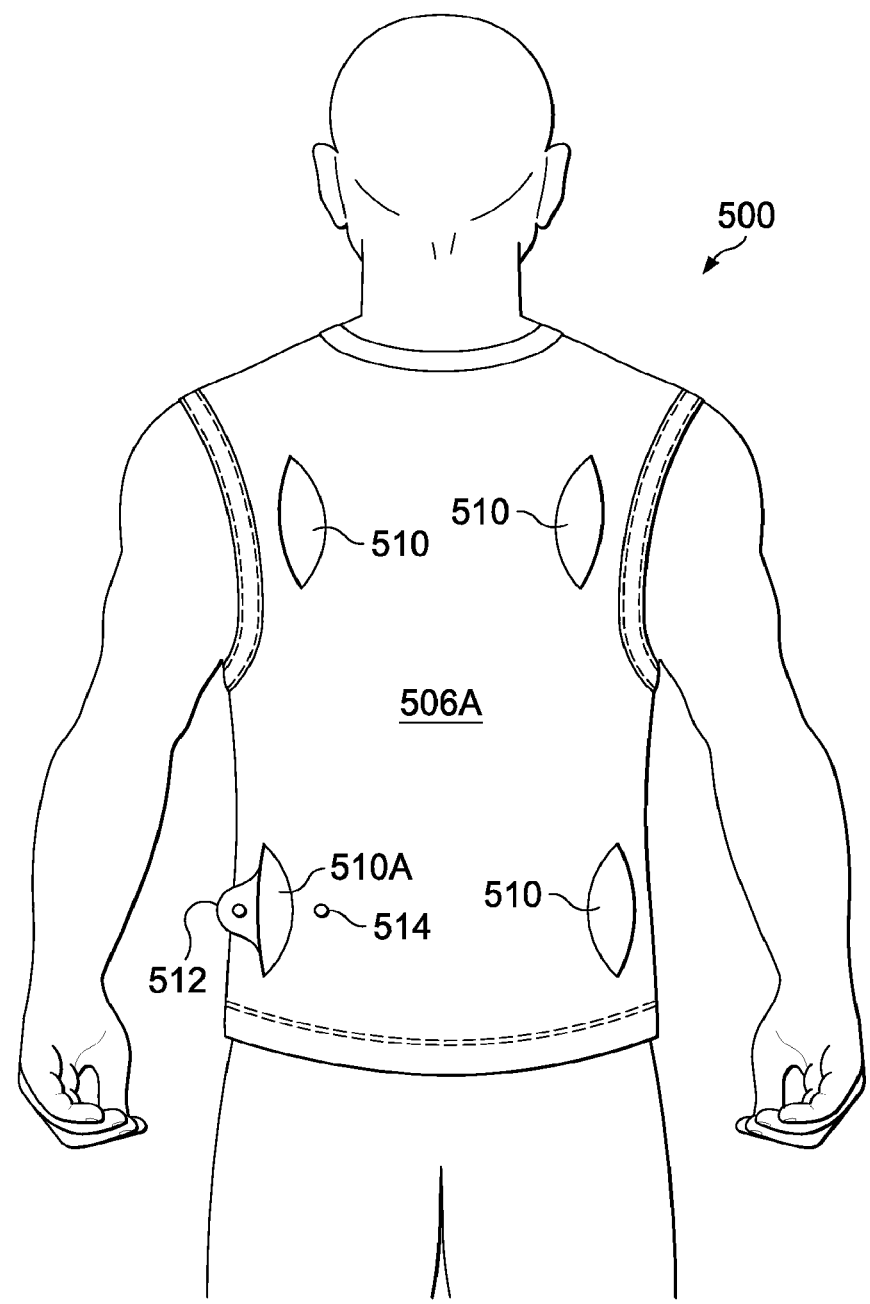
FIG. 12 is a rear-view of a medical apparatus according to one embodiment of the disclosure.

Referring now to FIG. 12, there is depicted a medical garment 500 that is similar in common respects to the above-described medical garments. Medical garment 500 can have some or all of the features described herein for medical garments, but which for conciseness will not be repeated for medical garment 500, which is shown to illustrate several useful features of medical garments herein and which can be used by patients, including infants, children, adolescents, adults and geriatric patients as well as their caregivers. There is shown a view of the back panel 506A of the medical garment 500 being worn by a patient, which can be an infant, a child, an adult, or a geriatric patent. The back panel 506A can be a relatively soft, flexible material of woven or nonwoven fibers. The back panel 506A can be a unitary, one-piece panel joined to the front panel at the sides and top. The back panel 506A can also be multi-piece, and can have openings and removable panels, as described on the front panel of various embodiments described herein. As shown in FIG. 12, another feature that can be implemented on embodiments of the medical garment 500 with some or all of the features described herein is at least one of an opening 510 on the side and/or back of the medical garment 500 to accommodate medical devices such as pumps and medical treatment bags, e.g., for infusions, that can be worn on the patient's back, such as in a backpack. Opening 510 can be positioned in any convenient location, including relatively low near the waist of the medical garment 500, or relatively high, near the arm openings of the medical garment 500, as indicated in FIG. 12. The location of opening 510 can be determined by the type of therapy a patient is undergoing, and the medical devices required. Therapy dependent patients can be infused through central line, a G-Tube, and/or a J-Tube, for various reasons, including for parenteral or enteral nutrition. Such infusions can take the majority of day in an ambulatory environment. In certain cases, nutrition can be infused from a G-line, a J-line, or a central line to a pump worn on the patient's back. Other various treatments can require medical treatments to be delivered through infusion pumps worn on the patient's back. Further, bags of medicine attached to the pumps can also be located on the patient's back, such as in a backpack. Patients need a way to discretely conceal tubes and protect catheters from dislodgment. Thus, opening(s) 510 can accommodate the protected passage of medical devices from, e.g., a backpack, to the medical garment 500, and, accordingly, secured near the patient's body.

Any opening 510 can be defined by the complete enclosure of a portion of the back panel 506A, as shown for opening 510 in FIG. 12. However, the opening can also be formed by a flap and snap arrangement as shown for opening 510A that can be closed into an opening by bringing flap 512 into a closed position with a closure, for example, a snap 514.

Figure 13:
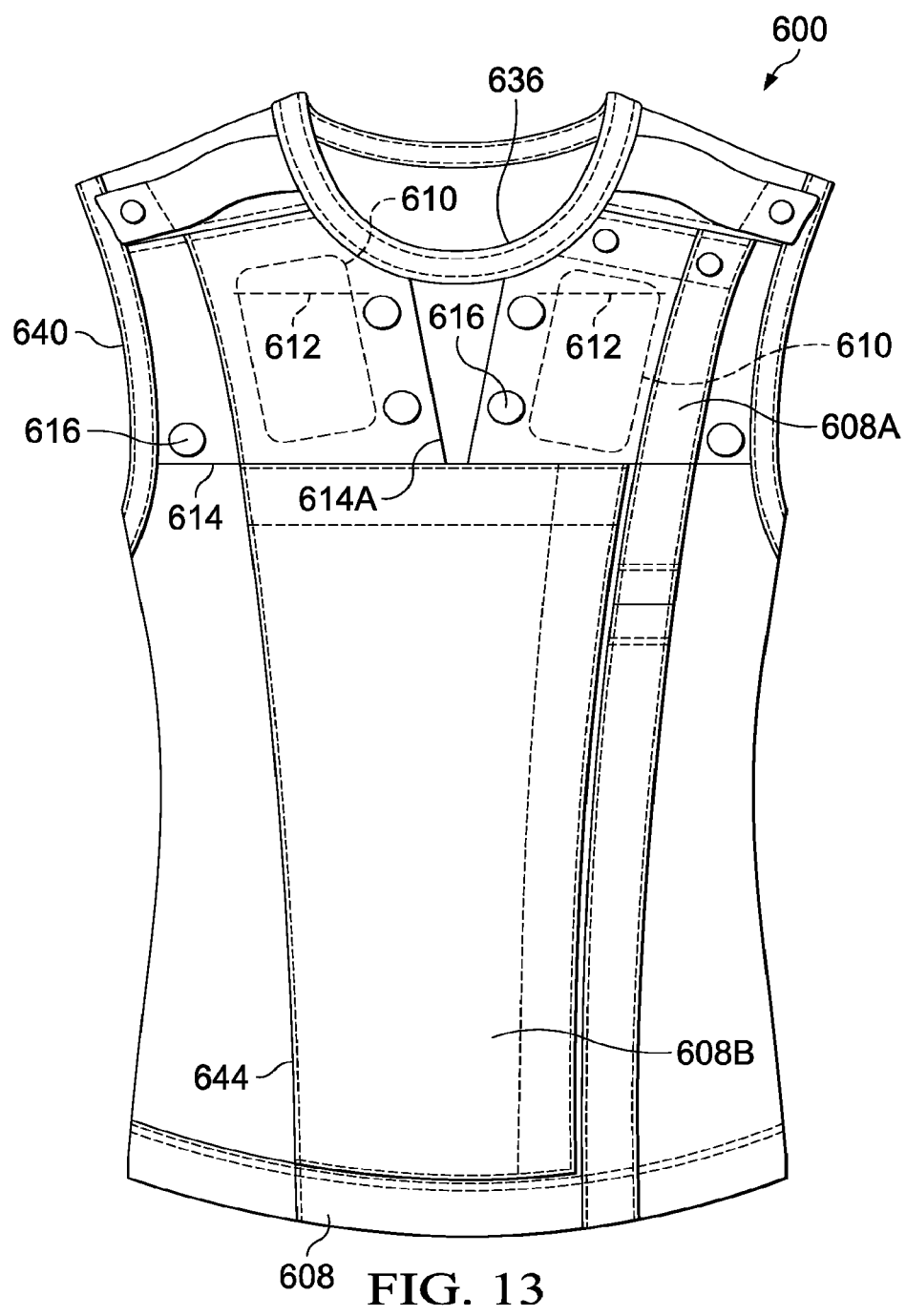
FIG. 13 is a representation of a medical apparatus according to one embodiment of the disclosure.

Referring now to FIG. 13, there is depicted a medical garment 600 that is similar in common respects to the above-described medical garments. Medical garment 600 can have some or all of the features described herein for medical garments, but which for conciseness will not be repeated for medical garment 600, which is shown to illustrate several useful features of medical garments herein and which can be used by patients, including infants, children, adolescents, adults and geriatric patients as well as their caregivers.

Medical garment 600 can be useful for securing various medical devices used by renal failure and/or dialysis patients, including infants, children, adolescents, adults and geriatric patients. The medical garment 600 can include features useful for vascular access for placement of tunneled dialysis catheters. For example, for hemodialysis the right internal jugular vein can be the preferred vascular access site for tunneled-cuffed central venous catheters. Likewise, the left internal jugular vein and subclavian veins may be accessed.

Medical garment 600 can have an outward facing surface 608 comprising two discrete panels, an upper panel 608A and a lower panel 608B, both attached to the front panel 606, and separately openable, for example about a seam 644 at which both the upper panel 608A and the lower panel 608B are attached to the front panel 606. Medical garment 600 can have an upper pocket 610 on one or both sides of the medical garment, positioned in a relatively high position, such as near the neckline 636 and/or one of an arm opening 640 on the upper panel 608A. By placing the upper pocket 610 near the neckline 636 and/or one of an arm opening 640, medical devices can be contained therein in relatively close proximity to the patient's left or right jugular vein (depending on the location of the upper pocket 610). Upper pocket 610 can be water resistant or water proof, and can secure a catheter which can exit the upper pocket 610 via a slit 612 to be routed to the patient.

Upper pocket 610 can include an outer flap secured to the front panel of the medical garment, and can include an arm opening portion 614 that extends to the arm opening 640 and/or neck opening portion 614A that extends to the neckline 636. The arm opening portion 614 and/or the neck opening portion 614A facilitate removal of the medical garment 600 without disconnecting any medical devices, such as infusion catheters that are contained in an upper pocket 610. Snap restraints 616 can be positioned on the upper pocket 610 to facilitate closing and opening of the upper pocket 610.

Figure 14:
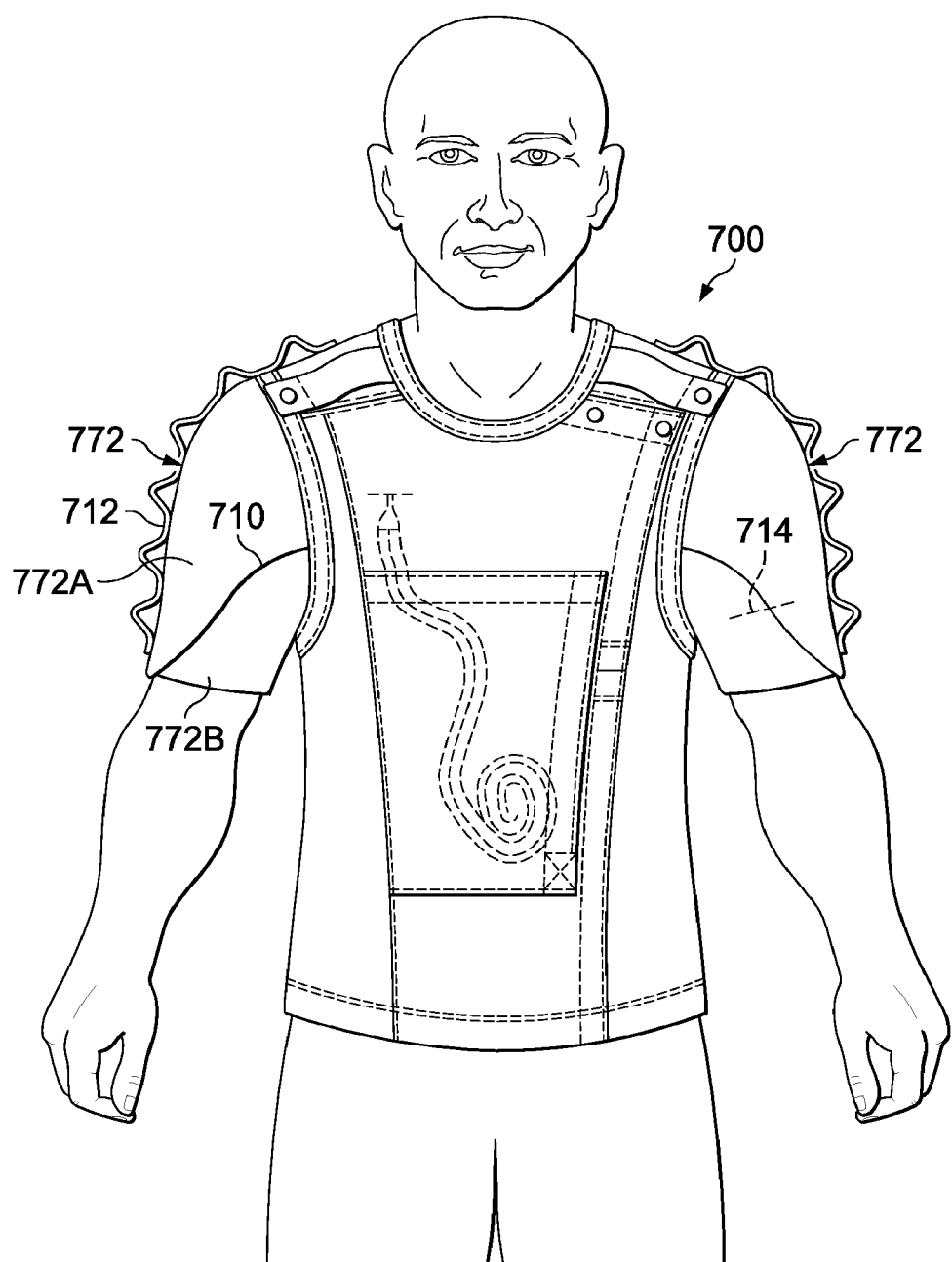
FIG. 14 is a representation of a medical apparatus according to one embodiment of the disclosure.

Referring now to FIG. 14, there is depicted a medical garment 700 that is similar in common respects to the above-described medical garments. Medical garment 700 can have some or all of the features described herein for medical garments, but which for conciseness will not be repeated for medical garment 700, which is shown to illustrate several useful features of medical garments herein and which can be used by patients, including infants, children, adolescents, adults and geriatric patients as well as their caregivers. Medical garment 700 can be useful for securing various medical devices associated with the use of a peripherally inserted central catheter line, i.e., a PICC line, including by an infant, child, adolescent, adult and geriatric patients. PICC lines can be appropriate when more than two weeks of treatment are needed, including for intravenous access that can be used for a prolonged period of time, chemotherapy regimens, antibiotic therapy, or total parenteral nutrition. Complications from the use of a PICC line can include blood clots, infection, and catheter occlusion. To decrease the risk of infection, management of the PICC line must adhere to strict infection control and securement procedures. A PICC line can be inserted in a peripheral vein in the arm. Securing the PICC line can help prevent post-insertion movements of the line, which otherwise could place the tip in an unsafe position, or otherwise lead to malposition and/or dislodgment.

The medical garment 700 can have a sleeve 772 with features useful for securing a catheter, including by way of example, a PICC line. The medical garment 700 can have a sleeve 772 that extends through an arm opening of the body portion. For example, the sleeve 772 can have a front sleeve portion 772A and a back sleeve portion 772B separated by a slit 710, and which can be tailored such that the front sleeve portion 772A and/or the back sleeve portion 772B can wrap, such as in a diagonal wrap, around the arm of the patient to allow a catheter to be constrained between front sleeve portion 772A and the back sleeve portion 772B. Thus, the catheter tubing can be secured through slit 710, such that the sleeve 772 secures the PICC line, which can be routed to an integrated and/or load bearing low profile anchor located in a pocket 720, as described in embodiments herein. Snaps 712 which can be sewn into sleeve 772, for example from a shoulder portion to the bottom of sleeve 772 can permit the sleeve to be opened without disconnection of the PICC line. In an embodiment, a separate interior slit 714 can be provided on sleeve 772 for use in routing a peripheral catheter from the outside of the sleeve 772 to the inside. In an embodiment, the PICC line can be threaded in the channels defined between the snaps 712 to help restrain the PICC line. In an embodiment, the sleeve 772 can comprise waterproof or water resistant material. In an embodiment, the front sleeve portion can be a discrete panel of the sleeve and can be wrappable around a portion of the back sleeve portion, which can also be a discrete panel of the sleeve. A PICC line can be wrapped, and thereby secured, between the front sleeve portion and the back sleeve portion. The discrete panels can be affixed to the body portion of the medical garment at their respective proximal ends.

Figure 15:
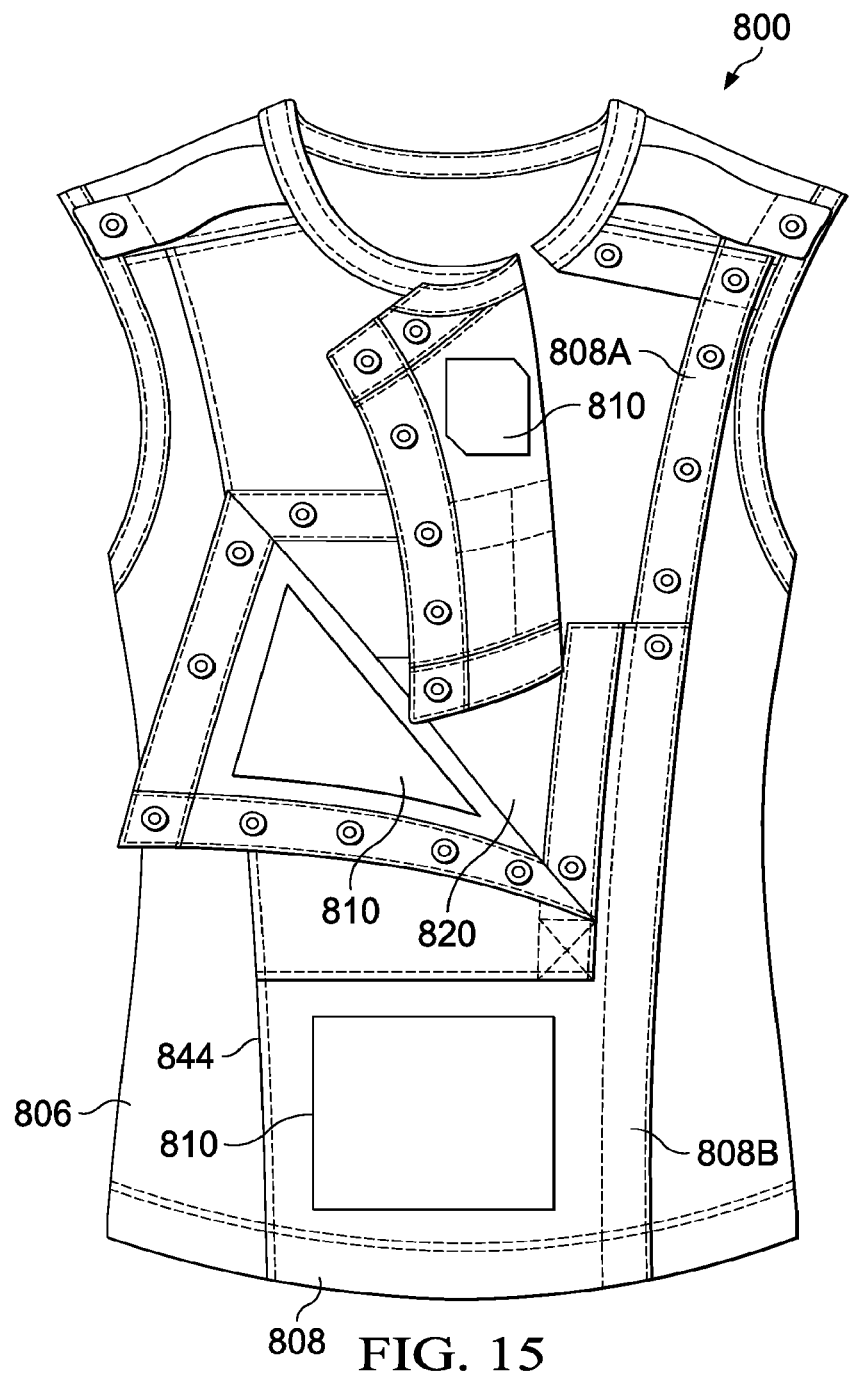
FIG. 15 is a representation of a medical apparatus according to one embodiment of the disclosure.

Referring now to FIG. 15, there is depicted a medical garment 800 that is similar in common respects to the above-described medical garments. Medical garment 800 can have some or all of the features described herein for medical garments, but which for conciseness will not be repeated for medical garment 800, which is shown to illustrate several useful features of medical garments herein and which can be used by patients, including infants, children, adolescents, adults and geriatric patients as well as their caregivers. The medical garment 800 can have an outward-facing surface 808 which can include two discrete panels, an upper panel 808A and a lower panel 808B, both attached to the front panel 806, and separately openable, for example about a seam 844 at which both the upper panel 808A and the lower panel 808B are attached to the front panel 806.

Medical garment 800 can have on one or more locations a writing surface 810. For example, a writing surface 810 can be disposed on one or more of a portion of the outward-facing surface 808, including on or inside upper panel 808A, on or inside lower panel 808B, or on or inside outer panel 818 attached to the outward-facing surface 808 of the front panel 806. The writing surface 810 can be on or inside a pocket 820, as described hereinabove. The writing surface 810 can be a relatively smooth, writable surface such as a thin, polymer film joined to the medical garment 800 as an integral writing surface, or it can be a discrete element, such as a piece of paper or a card that is slipped into a clear sleeve (not shown) which is joined to the medical garment 800. Information relevant to the care of the patient wearing the medical garment 800 can be written on the writing surface. Of course, by "written" in addition to handwriting, is meant the application of informational indicia by any known method, including, for example, printing out instructions by electronic means either directly or indirectly to the writing surface. Thus, a caregiver can write medications, allergies, surgery instructions or the like on the writing surface. In an embodiment, the writing surface 810 can facilitate writing by ink that glows in the dark, or otherwise is light sensitive to communicate even in low light conditions. The written information can include the level of care necessary, critical care instructions, surgical instructions, and the like.

Figure 16:
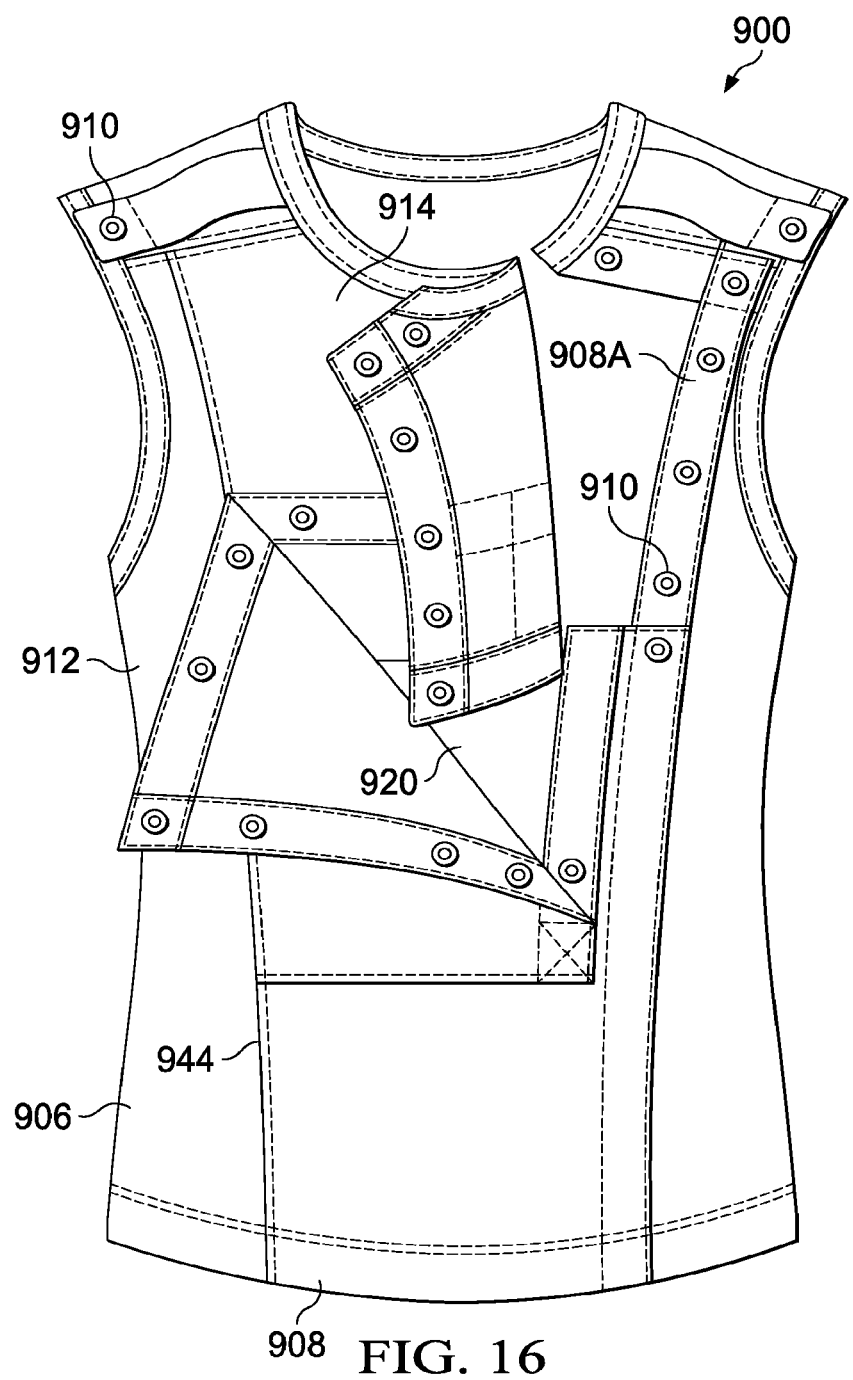
FIG. 16 is a representation of a medical apparatus according to one embodiment of the disclosure.

Referring now to FIG. 16, there is depicted a medical garment 900 that is similar in common respects to the above-described medical garments. Medical garment 900 can have some or all of the features described herein for medical garments, but which for conciseness will not be repeated for medical garment 900, which is shown to illustrate several useful features of medical garments herein and which can be used by patients, including infants, children, adolescents, adults and geriatric patients as well as their caregivers. The medical garment 900 can have an outward facing surface 908 which can include two discrete panels, an upper panel 908A and a lower panel 908B, both attached to the front panel 906, and separately openable, for example about a seam 944 at which both the upper panel 908A and the lower panel 908B are attached to the front panel 906.

Medical garment 900 can have various portions and components that are visually distinguishable in a manner that communicates to a patient or a caregiver something about the function of the various portions and components color-coded, with the color carrying an informative meaning. By color-coded is meant that if the medical garment is a first color, the color-coded component is a second color, different from the first color. For example, in an example, the medical garment can have one or more of the connection members, such as restraint snaps 910 color-coded. Likewise one or more of the panels 912 that make up the medical garment can be color-coded. Further, one or more of the openable portions, such as either of the upper panel 908A and a lower panel 908B can each be color-coded. All or portions of a pocket 920 can be color-coded.

Figure 17:
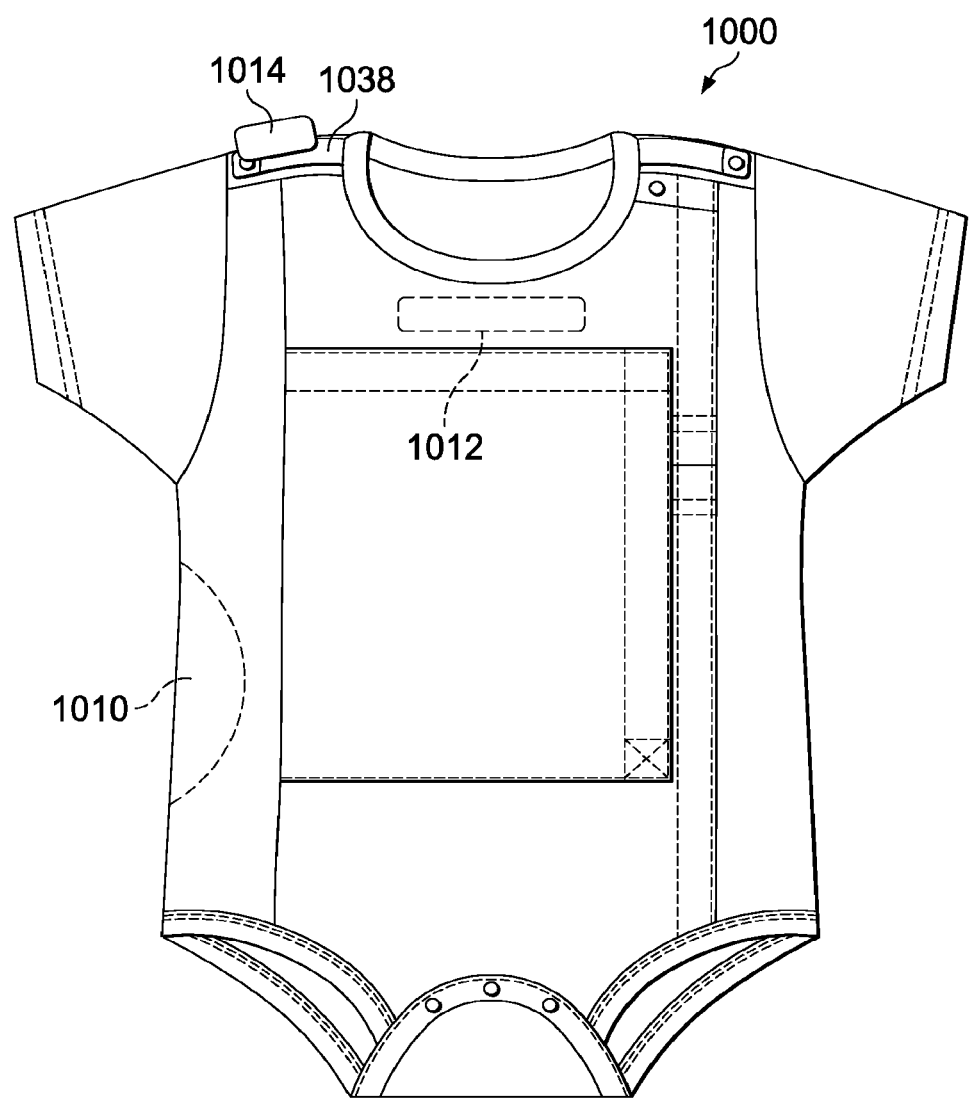
FIG. 17 is a representation of a medical apparatus according to one embodiment of the disclosure.

Referring now to FIG. 17, there is depicted a medical garment 1000 that is similar in common respects to the above-described medical garments. Medical garment 1000 can have some or all of the features described herein for medical garments, but which for conciseness will not be repeated for medical garment 1000, which is shown to illustrate several useful features of medical garments herein and which can be used by patients, including infants, children, adolescents, adults and geriatric patients as well as their caregivers. The medical garment 1000 can have integrated therein, such as by sewing, attaching, or otherwise joining, various components that take advantage of wireless communication for monitoring and tracking patient data in real time. For example, medical garment can have joined thereto one or more of a monitor 1010 that can monitor, record, and/or report to a remote electronic device, patient data, such as body temperature, blood pressure, heart rhythms, and vitals. In like manner, remote out patient information can be transmitted to a monitored location/ clinician. Further, a wireless patient tracker 1012 can monitor patient location and movements, such as detecting and assessing the severity of a fall. The wireless patient tracker 1012 can signal for help, and can utilize GPS technology to help locate the patient. Further, a remotely-connected device, such as monitor 1010 can be accessed remotely by a caregiver who can, for example, make adjustments to medical care, such as making adjustments to catheter-delivered medications. Any wireless technology can be employed, including Bluetooth®, internet, and near-field communication.

In an embodiment, medical garment 1000 can include a hearing aid member 1014. A hearing aid member 1014 can amplify sounds near the patient so that a hearing-impaired patient can more readily hear sounds, such as those of a caregiver providing instructions. In an embodiment the hearing aid member 1014 can be an assistive listening system from OTIC Inc. The hearing aid member 1014 can be integral with the medical garment, or it can be attached, such as by clipping to a portion of the medical garment 1000, such as on a shoulder portion, including a shoulder strap 1038.

For all embodiments of medical garments disclosed herein, various features can be employed. For example, the medical garment can be a single-use disposable garment, or it can be washable and reusable. The medical garment can utilize a coolant membrane on all or part of its external or internal surfaces to help, for example, reduce fever in a patient. The material of the medical garment can be charcoal infused. The material can have integrated therein components that aid in lowering low body temperature, treating hyperthermia, reducing trauma, detecting infection (such as with a fabric color change). The material can be liquid repellant. Various flaps and strips can be added to aid in managing wires and tubes to help a patient in crawling, walking, or sleeping. In general, all materials of the medical garment can be suitable for radiological scanners, such as MRI scanners, including all connection members, such as snaps, which can be made of plastic.

The use of a representative medical garment will now be described, with specific reference to a patient who already has a catheter tube 104 (as shown in FIG. 1) in place in their upper chest region along with a plurality of catheter tubes 104A (as shown in FIG. 5) extending away from the external hub of the catheter. Of course a similar procedure is followed when the garment is to be used with other medical devices, such as a Holter monitor wherein the electrical leads are positioned similar to the catheter tubing and the Holter unit itself stored within the pocket of the garment.

Using medical garment 100 as an example, with the medical garment 100 opened, the patient's arms are inserted into right and left arm openings 140, with the inner surface of back panel 106A against the patient's back. Lower panel 108B is then snapped closed. Next, the catheter tube 104 is positioned such that it extends downwardly past the lower edge of upper panel 108A, and either draped over lower panel 108B or inserted into the lower portion of pocket 120. The upper panel 108A is then snapped closed. Because the lower edge of upper panel 108A and upper edge of lower panel 108B are not affixed to one another, the catheter tubing will extend through access opening 146.

Next, the catheter tube 104 is positioned within the low profile anchor 112 in the manner described previously. If use of the catheter tubing is not necessary at that time, the catheter tubing extending from low profile anchor is merely inserted into the pocket 120 such as by coiling the tubing in the manner depicted in FIG. 1. The outer panel is then snapped closed with the catheter tubing stowed within the pocket 120. The garment itself helps to limit movement of the external portion of the central venous catheter by applying a gentle compressive force against the catheter. Similarly, the low profile anchor will also hold the catheter tubing in place, with the pocket further protecting the catheter tubing and preventing any pulling force from being applied to the tubing (whether inadvertently or from an infant or toddler pulling on the catheter tubing). The pocket also bears the weight of any catheter tubing (or other portion of a medical device) stored therein, thus providing additional strain relief. In this manner, the garment prevents pulling, dislodgement, breakage or other interference with the central venous catheter and tubing during normal daily activities or during sleep, thereby helping to reduce pain, inflammation, infection, and/or reduced catheter performance due to damaged tubing, breakage, catheter dislodgement and the like. Storing the catheter tubing out of sight, within the pocket not only aids in keeping the catheter tubing clean and safe, but also provides psychological benefits for some patients, since many, particularly children, can be embarrassed or otherwise uncomfortable if the catheter tubing is visible.

If use of the catheter tubing is necessary such as for the infusion of medication through the central venous catheter, the pocket is opened and the catheter tubing removed from the pocket (or at least as much as is necessary for infusion purposes). If desired, the tubing may be draped over one shoulder, beneath a shoulder strap 138, in order to maintain the tubing in a desired, out-of-the-way position, so as to minimize interference with, for example, other activities of the patient during infusion. Holding the tubing in a desired position using a shoulder strap is also advantageous for infusion while the patient is sleeping, helping to avoid the tubing becoming entangled with the patient or other apparatus should the patient move.

Of course the length, depth and width of the pocket may be altered, as desired. For example, the garment may be configured such that the pocket extends from adjacent the neck opening all the way to the bottom edge of the garment (i.e., the waist opening of the garment). Similarly, the relative lengths of the various panels may be varied in order to alter the vertical location of the access opening.

For example, in some embodiments the pocket extends at least about 25% of the length of the garment (measured from shoulder, at neck opening, to bottom edge, in other embodiments about 30-70% of the length of the garment, and in still other embodiments about 35-60% of the length of the garment. The vertical location of the access opening in some embodiments is below the arm openings, and in some embodiments within the upper half of the pocket. In still further embodiments, the vertical location of the access opening is between the lowermost extent of the arm openings and the vertical center of the garment.

It is noted that terms like "specifically," "preferably," "commonly," and "typically" are not utilized herein to limit the scope of the claimed disclosure or to imply that certain features are critical, essential, or even important to the structure or function of the claimed disclosure. Rather, these terms are merely intended to highlight alternative or additional features that may or may not be utilized in a particular embodiment of the present disclosure. It is also noted that terms like "substantially" and "about" are utilized herein to represent the inherent degree of uncertainty that may be attributed to any quantitative comparison, value, measurement, or other representation.

Having described the disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

All documents cited in the Detailed Description of the Disclosure are, in relevant part, incorporated herein by reference; the citation of any document is not to be construed as an admission that it is prior art with respect to the present disclosure. To the extent that any meaning or definition of a term in this written document conflicts with any meaning or definition of the term in a document incorporated by reference, the meaning or definition assigned to the term in this written document shall govern.

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

What is claimed is:

1. A medical apparatus, comprising:
    a. a garment, the garment comprising a body portion comprising an upper panel and a lower panel juxtaposed with the upper panel to define an access opening, the access opening providing access between the upper panel and the lower panel;
    b. an anchor secured on the body portion, the anchor configured for releasable securement of a first portion of a medical device; and
    c. an outer panel affixed to and selectively detachable from the body portion, the outer panel spanning at least a portion of the access opening and defining a selectively closeable pocket configured to retain a second portion of the medical device;
    wherein the garment comprises a sleeve affixed to the body portion at an arm opening, the sleeve defining an opening through which a third portion of the medical device extending through the arm opening can be routed and secured.

2. The medical apparatus of claim 1, wherein the garment comprises bamboo fiber.

3. The medical apparatus of claim 1, wherein a portion of the selectively closeable pocket is waterproof.

4. The medical apparatus of claim 1, wherein the anchor comprises a first strip member and a mating second strip member hingedly joined to the first strip member.

5. The medical apparatus of claim 1, wherein the anchor comprises a first strip member and a mating second strip member hingedly joined to the first strip member, and wherein the first strip member and the mating second strip member comprise a plurality of spaced apart joining locations and are releasably joinable at the plurality of spaced apart joining locations.

6. The medical apparatus of claim 1, wherein the anchor comprises a first strip member and a mating second strip member hingedly joined to the first strip member, and wherein the first strip member and the mating second strip member comprise a plurality of spaced apart joining locations and are releasably joinable at the plurality of spaced apart joining locations, and further wherein the anchor comprises a color coded portion, the color coded portion being a visual indication for communicating information relating to a type of the medical device being secured therein.

7. A medical apparatus, comprising:
    a. a garment, the garment comprising a body portion comprising an upper panel and a lower panel juxtaposed with the upper panel to define an access opening, the access opening providing access between the upper panel and the lower panel;

b. an anchor secured on the body portion, the anchor configured for releasable securement of a first portion of a medical device; and c. an outer panel affixed to and selectively detachable from the body portion, the outer panel spanning at least a portion of the access opening and defining a selectively closeable pocket configured to retain a second portion of the medical device;

wherein the garment comprises an arm opening and a sleeve affixed to the body portion at the arm opening, the sleeve comprising a first sleeve portion and a second sleeve portion, the first sleeve portion being wrappable over the second sleeve portion to define an opening between the first sleeve portion and the second sleeve portion through which a third portion of the medical device extending from the arm opening can be secured.

8. The medical apparatus of claim 7, wherein the garment comprises bamboo fiber.

9. The medical apparatus of claim 7, wherein a portion of the selectively closeable pocket is water-proof.

10. The medical apparatus of claim 7, wherein the anchor comprises a first strip member and a mating second strip member hingedly joined to the first strip member.

11. The medical apparatus of claim 7, wherein the anchor comprises a first strip member and a mating second strip member hingedly joined to the first strip member, and wherein the first strip member and the mating second strip member comprise a plurality of spaced apart joining locations and are releasably joinable at the plurality of spaced apart joining locations.

12. The medical apparatus of claim 7, wherein the anchor comprises a first strip member and a mating second strip member hingedly joined to the first strip member, and wherein the first strip member and the mating second strip member comprise a plurality of spaced apart joining locations and are releasably joinable at the plurality of spaced apart joining locations, and further wherein the anchor comprises a color coded portion, the color coded portion being a visual indication for communicating information relating to a type of the medical device being secured therein.

13. A medical apparatus, comprising:

a. a garment, the garment comprising a body portion comprising an upper panel and a lower panel juxtaposed with the upper panel to define an access opening, the access opening providing access between the upper panel and the lower panel;

b. an anchor affixed to the body portion, the anchor configured for releasable securement of a first portion of a medical device, wherein the anchor comprises a first woven fabric strip member and a mating second woven fabric strip member hingedly joined to the first woven fabric strip member, and wherein the first woven fabric strip member and the mating second woven fabric strip member comprise a plurality of spaced apart joining locations and are releasably joinable at the plurality of spaced apart joining locations; and c. an outer panel affixed to and selectively detachable from the body portion, the outer panel spanning at least a portion of the access opening and defining a selectively closeable pocket configured to retain a second portion of the medical device;

wherein the garment comprises a sleeve affixed to the body portion at an arm opening, the sleeve defining an opening through which a third portion of the medical device extending through the arm opening can be routed and secured.

14. The medical apparatus of claim 13, wherein the garment comprises bamboo fiber.

15. The medical apparatus of claim 13, wherein a portion of the selectively closeable pocket is water resistant.

16. The medical apparatus of claim 13, wherein the anchor comprises a first strip member and a mating second strip member hingedly joined to the first strip member, and wherein the first strip member and the mating second strip member comprise a plurality of spaced apart joining locations and are releasably joinable at the plurality of spaced apart joining locations, and further wherein the anchor comprises a color coded portion, the color coded portion being a visual indication for communicating information relating to a type of the medical device being secured therein.

17. The medical apparatus of claim 13, wherein the sleeve comprises water resistant material.

18. The medical apparatus of claim 13, further comprising a side retention strap.

19. The medical apparatus of claim 13, further comprising a sensor, the sensor comprising a transmitter for wireless transmission.

20. The medical apparatus of claim 13, wherein the sleeve comprises a first sleeve portion and a second sleeve portion, and the first sleeve portion comprises a discrete panel of the sleeve and is wrappable around the second sleeve portion.

\* \* \* \* \*